(12) United States Patent
Shuford et al.

(10) Patent No.: US 12,163,963 B2
(45) Date of Patent: Dec. 10, 2024

(54) METHODS AND SYSTEMS FOR LC-MS/MS PROTEOMIC GENOTYPING

(71) Applicant: Laboratory Corporation of America Holdings, Burlington, NC (US)

(72) Inventors: Christopher Michael Shuford, Mebane, NC (US); Russell Philip Grant, Chapel Hille, NC (US); Meghan Norris Bradley, Mebane, NC (US); Patricia Louise Miller Holland, High Point, NC (US); Michael Levandoski, Hillsborough, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 259 days.

(21) Appl. No.: 17/453,973

(22) Filed: Nov. 8, 2021

(65) Prior Publication Data

US 2022/0091131 A1    Mar. 24, 2022

Related U.S. Application Data

(63) Continuation of application No. 16/428,532, filed on May 31, 2019, now Pat. No. 11,199,547.

(60) Provisional application No. 62/679,133, filed on Jun. 1, 2018, provisional application No. 62/679,286, filed on Jun. 1, 2018, provisional application No. 62/680,256, filed on Jun. 4, 2018.

(51) Int. Cl.
| | |
|---|---|
| *G01N 33/68* | (2006.01) |
| *G01N 30/06* | (2006.01) |
| *G01N 30/34* | (2006.01) |
| *G01N 30/72* | (2006.01) |
| *G01N 30/02* | (2006.01) |

(52) U.S. Cl.
CPC ......... *G01N 33/6848* (2013.01); *G01N 30/06* (2013.01); *G01N 30/34* (2013.01); *G01N 30/7233* (2013.01); *G01N 33/6851* (2013.01); *G01N 2030/027* (2013.01); *G01N 2496/80* (2013.01); *G01N 2570/00* (2013.01); *G01N 2800/347* (2013.01)

(58) Field of Classification Search
None
See application file for complete search history.

(56) References Cited

U.S. PATENT DOCUMENTS

| | | |
|---|---|---|
| 5,772,874 A | 6/1998 | Quinn et al. |
| 5,795,469 A | 8/1998 | Quinn et al. |
| 5,919,368 A | 7/1999 | Quinn et al. |

(Continued)

FOREIGN PATENT DOCUMENTS

| | | |
|---|---|---|
| CN | 103649329 A | 3/2014 |
| CN | 105229024 A | 1/2016 |

(Continued)

OTHER PUBLICATIONS

U.S. Appl. No. 16/428,532, Final Office Action, Aug. 6, 2021, 10 pages.

(Continued)

*Primary Examiner* — Xiaoyun R Xu
(74) *Attorney, Agent, or Firm* — Kilpatrick Townsend & Stockton LLP

(57) ABSTRACT

Disclosed are methods and systems using liquid chromatography/tandem mass spectrometry (LC-MS/MS and 2D-LC-MS/MS) for the proteomic analysis of genotypes. In certain embodiments, samples used in the analysis comprise dried bodily fluids.

20 Claims, 14 Drawing Sheets
Specification includes a Sequence Listing.

(56) References Cited

U.S. PATENT DOCUMENTS

| | | | |
|---|---|---|---|
| 5,968,367 | A | 10/1999 | Quinn et al. |
| 6,107,623 | A | 8/2000 | Bateman et al. |
| 7,070,949 | B2 | 7/2006 | Suckau et al. |
| 7,473,892 | B2 | 1/2009 | Sano et al. |
| 8,658,396 | B2 | 2/2014 | Turner et al. |
| 9,347,084 | B2 | 5/2016 | Turner et al. |
| 11,199,547 | B2 | 12/2021 | Shuford et al. |
| 2005/0042676 | A1 | 2/2005 | Hamon et al. |
| 2006/0094121 | A1 | 5/2006 | Reid et al. |
| 2016/0290901 | A1 | 10/2016 | Dick et al. |

FOREIGN PATENT DOCUMENTS

| | | |
|---|---|---|
| EP | 1356121 | 10/2003 |
| EP | 1844338 | 10/2007 |
| EP | 3139171 | 3/2017 |
| EP | 3163303 A1 | 5/2017 |
| JP | 2008529027 | 7/2008 |
| WO | 02/061047 | 8/2002 |
| WO | 2006/082389 | 8/2006 |
| WO | 2012024189 A2 | 2/2012 |
| WO | 2012068642 A1 | 5/2012 |
| WO | 2012171560 A1 | 12/2012 |
| WO | 2014145275 A1 | 9/2014 |
| WO | 2016/025726 A1 | 2/2016 |
| WO | 2017/173390 | 10/2017 |

OTHER PUBLICATIONS

U.S. Appl. No. 16/428,532, Non-Final Office Action, Apr. 2, 2021, 11 pages.
U.S. Appl. No. 16/428,532, Notice of Allowance, Oct. 14, 2021, 9 pages.
U.S. Appl. No. 16/428,532, Supplemental Notice of Allowability, Oct. 21, 2021, 2 pages.
CA 3,101,500, Office Action, Nov. 2, 2021, 5 pages.
JP 2020-566642, Office Action, Feb. 24, 2022, 9 pages.
CA 3, 101,500, Office Action, Jun. 3, 2022, 6 pages.
JP 2020-566642, Notice of Allowance, Jun. 2, 2022, 4 pages.
Chambers et al., "Comparison of Proteins in Whole Blood and Dried Blood Spot Samples by LC/MS/MS", Journal of the American Society for Mass Spectrometry, vol. 24, No. 9, 2013, pp. 1338-1345.
Chen, Y. et al., "Simultaneous Phenotyping and Quantification of 1-1-Antitrypsin by Liquid Chromatography-Tandem Mass Spectrometry," Clin. Chem. 57(8):1161-1168 (2011).
Dufresne, J. et al., "Freeze-dried plasma proteins are stable at room temperature for at least 1 year," Clin. Proteom. 14:35 (2017) 14 pages.
Eng, J. et al., "An Approach to Correlate Tandem Mass Spectral Data of Peptides with Amino Acid Sequences in a Protein Database," J. Am. Soc. Mass. Spectrom. 5:976-989 (1994).
Gerber, S. et al., "Absolute quantification of proteins and phosphoproteins from cell lysates by tandem MS," Proc. Natl. Acad. Sci. 100(12):6940-6945 (2003).
Hu et al., "The Orbitrap: a new mass spectrometer", Journal of Mass Spectrometry, vol. 40, 2005, pp. 430-443.
Lim, A. et al., "Characterization of Transthyretin Variants in Familial Transthyretin Amyloidosis by Mass Spectrometric Peptide Mapping and DNA Sequence Analysis," Anal. Chem. 74:741-751 (2002).
Martin et al., "Dried Blood Spot Proteomics: Surface Extraction of Endogenous Proteins Coupled with Automated Sample Preparation and Mass Spectrometry Analysis", Journal of the American Society for Mass Spectrometry, vol. 24, No. 8, 2013, pp. 1242-1249.
Mayya, V. et al., "Absolute Quantification of Multisite Phosphorylation by Selective Reaction Monitoring Mass Spectrometry," Molecular & Cellular Proteomics 5:1146-1157 (2006).
Moat, S. et al., "Newborn screening for sickle cell disorders using tandem mass spectrometry: three years' experience of using a protocol to detect only the disease states," Annals of Clin. Biochem 54(5):601-611 (2017).
Nepomuceno, A. et al., "Detection of Genetic Variants of Transthyretin by Liquid Chromatography-Dual Electrospray Ionization Fourier-Transform Ion-Cyclotron-Resonance Mass Spectrometry," Clin. Chem. 50(9):1535-1543 (2004).
Nesvizhskii, A. et al., "A Statistical Model for Identifying Proteins by Tandem Mass Spectrometry," Anal. Chem. 75:4646-4658 (2003).
Rosting et al., "High Field Asymmetric Waveform Ion Mobility Spectrometry in Nontargeted Bottom-up Proteomics of Dried Blood Spots", Journal of Proteome Research, vol. 17, No. 6, 2018, 8 pages.
Steen, H. and Mann, M., "The ABC's (and XYZ's) of Peptide Sequencing," Nat. Rev. Mol. Cell Biol. 5(9):699-711 (2004).
Wilson et al., "An LC-MS/MS-Based Method for the Quantification of Pyridox(am)ine 5'-Phosphate Oxidase Activity in Dried Blood Spots from Patients with Epilepsy", Analytical Chemistry, vol. 89, No. 17, 2017, pp. 8892-8900.
Wolters, D. et al., An Automated Multidimensional Protein Identification Technology for Shotgun Proteomics, Anal. Chem. 73:5683-5690 (2001).
Yost et al., Chapter 8 in "Tandem Quadrupole Mass Spectrometry", 1983, pp. 175-195.
Zhou et al., "Rapid Detection and Quantification of Apolipoprotein L1 Genetic Variants and Total Levels in Plasma by Ultra-Performance Liquid Chromatography/Tandem Mass Spectrometry", Rapid Communications in Mass Spectrometry, vol. 27, Issue 23, Dec. 2013, pp. 2639-2647.
Zimmer et al., "Comparison of turbulent-flow chromatography with automated solid-phase extraction in 96-well plates and liquid-liquid extraction used as plasma sample preparation techniques for liquid chromatography-tandem mass spectrometry", Journal of Chromatography A., vol. 854, 1999, pp. 23-35.
PCT/US2019/034976 , "International Search Report and Written Opinion", Sep. 27, 2019, 14 pages.
PCT/US2019/034976, International Preliminary Report on Patentability, Dec. 10, 2020, 14 pages.
Application No. CA3,101,500 , Office Action, Mailed on Oct. 27, 2023, 8 pages.
Application No. CN201980036361.2 , Office Action, Mailed on Jul. 27, 2023, 26 pages.
Boemer, F. et al., "Newborn Screening for Sickle Cell Disease Using Tandem Mass Spectrometry," Clinical Chemistry 54(2):2037-2041 (2008).
Bradley, M. et al., "Quality Over Quantity: a Qualitative, Targeted Bottom-up Proteomics Approach to Genotyping Ape Lipoprotein L1," Clinical Biochemistry vol. 82:58-65 (2020).
Edwards, R. et al., "Top-down Proteomics and Direct Surface Sampling of Neonatal Dried Blood Spots: Diagnosis of Unknown Hemoglobin Variants," J. Am. Mass Spectrom. 23(11):1921-1930 (2012).
CA 3,101,500, Office Action, Jan. 12, 2023, 8 pages.
EP 19739421.6, Office Action, Mar. 15, 2023, 6 pages.

Variant Specific Surrogate Peptides

Wild-type
SEQ ID NO. 1

```
  1 MEGAALLRVS VLCIWMSALF LGVGVRAEEA GARVQQNVPS GTDTGDPQSK PLGDWAAGTM  60
 61 DPESSIFIED AIKYFKEKVS TQNLLLLITD NEAWNGFVAA AELPRNEADE LRKALDNLAR 120
121 QMIMKDKNWH DKGQQYRNMF LKEFPRLKSE LADGVQKVHK GTTIANVVSG 180
181 SLSISSGILT LVGMGLAPFT EGGSLVLLEP GMELGITAAL TGITSSTMDY GKKWWTQAQA 240
241 HDLVIKSLDK LKEVREFLGE NISNFLSLAG NTYQLTRGIG KDIRALRRAR ANLQSVPHAS 300
301 ASRPRVTEFI SAESGEQVER VNEPSILEMS RGVK░░░░░ V░░░░░░░░ ░░░░░░HLH 360
361 EGAKSETAEE LKKVAQELEE K░░░░░░░ ILQADQEL 398
```

"WT Peptide"
LNILNNYK

G1 allele
S342G
I384M
SEQ ID NO. 2

```
  1 MEGAALLRVS VLCIWMSALF LGVGVRAEEA GARVQQNVPS GTDTGDPQSK PLGDWAAGTM  60
 61 DPESSIFIED AIKYFKEKVS TQNLLLLITD NEAWNGFVAA AELPRNEADE LRKALDNLAR 120
121 QMIMKDKNWH DKGQQYRNMF LKEFPRLKSE LADGVQKVHK GTTIANVVSG 180
181 SLSISSGILT LVGMGLAPFT EGGSLVLLEP GMELGITAAL TGITSSTMDY GKKWWTQAQA 240
241 HDLVIKSLDK LKEVREFLGE NISNFLSLAG NTYQLTRGIG KDIRALRRAR ANLQSVPHAS 300
301 ASRPRVTEFI SAESGEQVER VNEPSILEMS RGVK░░░░░ V░░░░░░░░ ░░░░░░HLH 360
361 EGAKSETAEE LKKVAQELEE K░░LNNY░K ILQADQEL 398
```

"G1 Peptide"
LNKLNNYK

G2 allele
N388_Y389del
SEQ ID NO. 3

```
  1 MEGAALLRVS VLCIWMSALF LGVGVRAEEA GARVQQNVPS GTDTGDPQSK PLGDWAAGTM  60
 61 DPESSIFIED AIKYFKEKVS TQNLLLLITD NEAWNGFVAA AELPRNEADE LRKALDNLAR 120
121 QMIMKDKNWH DKGQQYRNMF LKEFPRLKSE LADGVQKVHK GTTIANVVSG 180
181 SLSISSGILT LVGMGLAPFT EGGSLVLLEP GMELGITAAL TGITSSTMDY GKKWWTQAQA 240
241 HDLVIKSLDK LKEVREFLGE NISNFLSLAG NTYQLTRGIG KDIRALRRAR ANLQSVPHAS 300
301 ASRPRVTEFI SAESGEQVER VNEPSILEMS RGVK░░░░░ V░░░░░░░░ ░░░░░░RHLH 360
361 EGAKSETAEE LKKVAQELEE K░░░░░░░░ ILQADQEL 398
```

"G2 Peptide"
LNILNK

FIG. 1

Common Surrogate Peptides

"Qualifying Peptide 1"

"Qualifying Peptide 2"

Wild-type
SEQ ID NO. 1

```
  1 MEGAALLRVS VLCIWMSALF LGVGVRAEEA GARVQQNVPS GTDTGDPQSK PLGDWAAGTM  60
 61 DPESSIFIED AIKYFKEKVS TQNLLLLLTD NEAWNGFVAA AELPRNEADE LRKALDNLAR 120
121 QMIMKDKNWH DKGQQYRNWF LKEFPRLKSE LEDNIRRLRA LADGVQKVHK GTTIANVVSG 180
181 SLSISSGILT LVGMGLAPFT EGGSLVLLEP GMELGITAAL TGITSSTMDY GKKWWTQAQA 240
241 HDLVIKSLDK LKEVREFLGE NISNFLSLAG NTYQLTRGIG KDIRALRRAR ANLQSVPHAS 300
301 ASRPRVTEPI SAESGEQVER VNEPSILEMS RGVKLHDVAE YFFIVLDWV SI          360
361 EGAK                                                             398
        ILQADQEL
```

G1 allele
S342G
I384M

SEQ ID NO. 2

```
  1 MEGAALLRVS VLCIWMSALF LGVGVRAEEA GARVQQNVPS GTDTGDPQSK PLGDWAAGTM  60
 61 DPESSIFIED AIKYFKEKVS TQNLLLLLTD NEAWNGFVAA AELPRNEADE LRKALDNLAR 120
121 QMIMKDKNWH DKGQQYRNWF LKEFPRLKSE LEDNIRRLRA LADGVQKVHK GTTIANVVSG 180
181 SLSISSGILT LVGMGLAPFT EGGSLVLLEP GMELGITAAL TGITSSTMDY GKKWWTQAQA 240
241 HDLVIKSLDK LKEVREFLGE NISNFLSLAG NTYQLTRGIG KDIRALRRAR ANLQSVPHAS 300
301 ASRPRVTEPI SAESGEQVER VNEPSILEMS RGVKLHDVAE YFFIVLDWV MIYTESKHLH  360
361 EGAK ILQADQEL                                                    398
```

G2 allele
N388_Y389del

SEQ ID NO. 3

```
  1 MEGAALLRVS VLCIWMSALF LGVGVRAEEA GARVQQNVPS GTDTGDPQSK PLGDWAAGTM  60
 61 DPESSIFIED AIKYFKEKVS TQNLLLLLTD NEAWNGFVAA AELPRNEADE LRKALDNLAR 120
121 QMIMKDKNWH DKGQQYRNWF LKEFPRLKSE LEDNIRRLRA LADGVQKVHK GTTIANVVSG 180
181 SLSISSGILT LVGMGLAPFT EGGSLVLLEP GMELGITAAL TGITSSTMDY GKKWWTQAQA 240
241 HDLVIKSLDK LKEVREFLGE NISNFLSLAG NTYQLTRGIG KDIRALRRAR ANLQSVPHAS 300
301 ASRPRVTEPI SAESGEQVER VNEPSILEMS RGVKLHDVAE SFIVLDWV IYTESKHLH    360
361 EGAK ILQADQEL                                                    398
```

FIG. 2

| Allele 1 | Allele 2 | Surrogate Peptide Detection Pattern | | | | | |
|---|---|---|---|---|---|---|---|
| | | "Qualifying Peptide 1" STATELY | "Qualifying Peptide 2" VAQLPLY | "G2 Peptide" NLNN_K | "G1 Peptide" LN_NNYK | "WT Peptide" LNLNNYK |
| WT | WT | Y | Y | | | Y |
| G1 | G1 | Y | Y | | Y | |
| G2 | G2 | Y | Y | Y | | |
| WT | G1 | Y | Y | | Y | Y |
| WT | G2 | Y | Y | Y | | Y |
| G1 | G2 | Y | Y | Y | Y | |

FIG. 6

| Genotype by Sanger Sequencing | N | Agreement by LC-MS/MS | |
|---|---|---|---|
| | | Liquid Plasma | Dry Plasma |
| WT/WT | 82 | 100% | 100% |
| WT/G1 | 64 | 100% | 100% |
| WT/G2 | 38 | 100% | 100% |
| G1/G1 | 10 | 100% | 100% |
| G1/G2 | 10 | 100% | 100% |
| G2/G2 | 5 | 100% | 100% |
| Total | 209 | 100% | 100% |

FIG. 9

SEQUENCE LISTING

```
<160> NUMBER OF SEQ ID NOS: 18

<210> SEQ ID NO 1
<211> LENGTH: 398
<212> TYPE: PRT
<213> ORGANISM: Homo sapiens

<400> SEQUENCE: 1

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
            85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Glu Leu Glu Asp Asn Ile Arg Arg Leu Arg Ala
145                 150                 155                 160
```

```
Leu Ala Asp Gly Val Gln Lys Val His Lys Gly Thr Thr Ile Ala Asn
                165                 170                 175
Val Val Ser Gly Ser Leu Ser Ile Ser Ser Gly Ile Leu Thr Leu Val
            180                 185                 190
Gly Met Gly Leu Ala Pro Phe Thr Glu Gly Gly Ser Leu Val Leu Leu
        195                 200                 205
Glu Pro Gly Met Glu Leu Gly Ile Thr Ala Ala Leu Thr Gly Ile Thr
    210                 215                 220
Ser Ser Thr Met Asp Tyr Gly Lys Lys Trp Thr Gln Ala Gln Ala
225                 230                 235                 240
His Asp Leu Val Ile Lys Ser Leu Asp Lys Leu Lys Glu Val Arg Glu
                245                 250                 255
Phe Leu Gly Glu Asn Ile Ser Asn Phe Leu Ser Leu Ala Gly Asn Thr
            260                 265                 270
Tyr Gln Leu Thr Arg Gly Ile Gly Lys Asp Ile Arg Ala Leu Arg Arg
        275                 280                 285
Ala Arg Ala Asn Leu Gln Ser Val Pro His Ala Ser Ala Ser Arg Pro
    290                 295                 300
Arg Val Thr Glu Pro Ile Ser Ala Glu Ser Gly Glu Gln Val Glu Arg
305                 310                 315                 320
Val Asn Glu Pro Ser Ile Leu Glu Met Ser Arg Gly Val Lys Leu Thr
                325                 330                 335
Asp Val Ala Pro Val Ser Phe Phe Leu Val Asp Val Val Tyr Leu
            340                 345                 350
Val Tyr Glu Ser Lys His Leu His Glu Gly Ala Lys Ser Glu Thr Ala
        355                 360                 365
Glu Glu Leu Lys Lys Val Ala Gln Glu Leu Glu Lys Leu Asn Ile
    370                 375                 380
Leu Asn Asn Asn Tyr Lys Ile Leu Gln Ala Asp Gln Glu Leu
385                 390                 395

<210> SEQ ID NO 2
<211> LENGTH: 398
<212> TYPE: PRT
<213> ORGANISM: Homo sapiens

<400> SEQUENCE: 2

Met Glu Gly Ala Ala Leu Leu Arg Val Ser Val Leu Cys Ile Trp Met
1               5                   10                  15
Ser Ala Leu Phe Leu Gly Val Gly Val Arg Ala Glu Glu Ala Gly Ala
            20                  25                  30
Arg Val Gln Gln Asn Val Pro Ser Gly Thr Asp Thr Gly Asp Pro Gln
        35                  40                  45
Ser Lys Pro Leu Gly Asp Trp Ala Ala Gly Thr Met Asp Pro Glu Ser
    50                  55                  60
Ser Ile Phe Ile Glu Asp Ala Ile Lys Tyr Phe Lys Glu Lys Val Ser
65                  70                  75                  80
Thr Gln Asn Leu Leu Leu Leu Thr Asp Asn Glu Ala Trp Asn Gly
                85                  90                  95
Phe Val Ala Ala Ala Glu Leu Pro Arg Asn Glu Ala Asp Glu Leu Arg
            100                 105                 110
Lys Ala Leu Asp Asn Leu Ala Arg Gln Met Ile Met Lys Asp Lys Asn
        115                 120                 125
Trp His Asp Lys Gly Gln Gln Tyr Arg Asn Trp Phe Leu Lys Glu Phe
    130                 135                 140
```

```
Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Gly Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Met
    370                 375                 380

Leu Asn Asn Asn Tyr Lys Ile Leu Gln Ala Asp Gln Glu Leu
385                 390                 395

<210> SEQ ID NO 3
<211> LENGTH: 396
<212> TYPE: PRT
<213> ORGANISM: Homo sapiens

<400> SEQUENCE: 3

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
                20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
        50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110
```

```
Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
        130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
    370                 375                 380

Leu Asn Asn Lys Ile Leu Gln Ala Asp Gln Glu Leu
385                 390                 395

<210> SEQ ID NO 4
<211> LENGTH: 9
<212> TYPE: PRT
<213> ORGANISM: Artificial Sequence
<220> FEATURE:
<223> OTHER INFORMATION: Synthentic Construct

<400> SEQUENCE: 4

Leu Asn Ile Leu Asn Asn Asn Tyr Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 5

Leu Asn Met Leu Asn Asn Asn Tyr Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Contstruct

<400> SEQUENCE: 6

Leu Asn Ile Leu Asn Asn Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Ser Glu Thr Ala Glu Glu Leu Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Val Ala Gln Glu Leu Glu Glu Lys
1               5

<210> SEQ ID NO 9
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9
cgacctggtc atcaaaagcc ttgac                                           25

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
ggaggcagag cttgcagtga gctg                                            24

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
agacgagcca gagccaatc                                                    19

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ctgccaggca tatctctcct                                                   20

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Asn Asn Tyr Lys
1

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: L = [15N, 13C6]-Leucine
<220> FEATURE:
<221> NAME/KEY: MISC_FEATURE
<222> LOCATION: (8)..(8)
<223> OTHER INFORMATION: K = [15N2, 13C6]-Lysine

<400> SEQUENCE: 14

Ser Glu Thr Ala Glu Glu Leu Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: L = [15N, 13C6]-Leucine
<220> FEATURE:
<221> NAME/KEY: MISC_FEATURE
<222> LOCATION: (8)..(8)
<223> OTHER INFORMATION: K = [15N2, 13C6]-Lysine

<400> SEQUENCE: 15

Val Ala Gln Glu Leu Glu Glu Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

```
<220> FEATURE:
<221> NAME/KEY: MISC_FEATURE
<222> LOCATION: (1)..(1)
<223> OTHER INFORMATION: L = [15N, 13C6]-Leucine
<220> FEATURE:
<221> NAME/KEY: MISC_FEATURE
<222> LOCATION: (9)..(9)
<223> OTHER INFORMATION: K = [15N2, 13C6]-Lysine

<400> SEQUENCE: 16

Leu Asn Ile Leu Asn Asn Asn Tyr Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L = [15N, 13C6]-Leucine
<220> FEATURE:
<221> NAME/KEY: MISC_FEATURE
<222> LOCATION: (9)..(9)
<223> OTHER INFORMATION: K = [15N2, 13C6]-Lysine

<400> SEQUENCE: 17

Leu Asn Met Leu Asn Asn Asn Tyr Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: L = [15N, 13C6]-Leucine
<220> FEATURE:
<221> NAME/KEY: MISC_FEATURE
<222> LOCATION: (7)..(7)
<223> OTHER INFORMATION: K = [15N2, 13C6]-Lysine

<400> SEQUENCE: 18

Leu Asn Ile Leu Asn Asn Lys
1               5
```

METHODS AND SYSTEMS FOR LC-MS/MS PROTEOMIC GENOTYPING

RELATED APPLICATIONS

This application is a continuation of U.S. patent application Ser. No. 16/428,532, filed May 31, 2019, which claims the benefit of and priority to U.S. Provisional Patent Application No. 62/679,133, filed Jun. 1, 2018, U.S. Provisional Patent Application No. 62/679,286, filed Jun. 1, 2018, and U.S. Provisional Patent Application No. 62/680,256, filed Jun. 4, 2018. These applications are each incorporated herein by reference in their entireties.

FIELD OF INVENTION

The presently disclosed subject matter relates to methods and systems for LC-MS/MS proteomic genotyping.

BACKGROUND

There is often a need in the medical field to determine the genotype at a particular genetic locus. For example, two genetic variants of Apo lipoprotein L1 (ApoL1), termed G1 and G2, are present in a large fraction of the African American population. Individuals possessing two ApoL1 risk variants (G1/G1, G2/G2, or G1/G2) are at an increased risk of developing non-diabetic kidney disease. Further, it has been demonstrated that kidney transplant recipients experience earlier allograft failure on average when using donor organs from African Americans with two ApoL1 risk variants. Protein sequencing by proteomic methods may identify genotypes by identifying the corresponding protein variant coded by the gene of interest, which can have practical benefits relative to conventional gene (DNA) sequencing and transcript (RNA) sequencing. This may be accomplished by proteomic analysis of the body fluid containing the protein variant; however, production of dry specimens from bodily fluids for proteomic analysis may be preferred when remote or self-sample collection is advantageous.

SUMMARY

In some embodiments, the presently disclosed subject matter provides methods and systems for the proteomic determination of a genotype of interest in a sample. The method may be embodied in a variety of ways.

For example, disclosed is a method for determining the genotype of a gene of interest in a subject, the method comprising: providing a biological sample from the subject; and using mass spectrometry to detect at least one allele specific surrogate peptide present in the sample; and determining the genotype based on the at least one allele specific surrogate peptide (i.e., the proteomic profile). In an embodiment, the method may comprise providing a body fluid from a subject, wherein the bodily fluid contains a protein derived from the gene of interest; depositing the body fluid on a solid substrate, wherein the fluid is allowed to dry to produce a dry specimen; digesting the dry specimen to generate at least one allele specific surrogate peptide; determining the genotype of the body fluid based on the presence or absence of the at least one allele specific surrogate peptide (i.e., the proteomic profile) by mass spectrometry. In an embodiment, the mass spectrometry comprises liquid chromatography tandem mass spectrometry (LC-MS/MS). In some embodiments, the liquid chromatography comprises high performance liquid chromatography (HPLC).

The method may include the step of digesting a protein or peptides derived from the gene of interest in the biological sample to generate allele specific surrogate peptides specific to the protein variant coded by the allele (i.e., genotype), wherein the surrogate peptides comprise a proteomic profile. In certain embodiments, the method may further comprise detecting the presence of at least one common surrogate peptide that is common to all protein variants coded by the alleles of the gene of interest. Thus, in certain embodiments, the protease digestion may produce common surrogate peptides (or qualifying peptides) that are common to the various alleles present for the gene. In an embodiment, the presence or absence of the at least one allele-specific surrogate peptide is determined by comparing a measured response for at least one allele-specific surrogate peptide to a measured response for at least one common surrogate peptide.

In some embodiments, the digestion step may be performed using the protease trypsin. Or, other proteases or chemicals for protein hydrolysis can be used. Also, in some embodiments, the protein derived from the gene of interest is denatured prior to digestion to facilitate digestion.

In some embodiments, an internal standard(s) may be used for the detected peptide or peptides. For example, the presence or absence of the allele specific surrogate peptides specific to a genotype may be determined by comparing the measured responses of the surrogate peptide to the responses of its internal standard added to the individual's sample. In some embodiments, the internal standard is a stable isotope-labeled analogue of the allele specific surrogate peptide. Additionally and/or alternatively, the presence or absence of the at least one common surrogate peptide may be determined by comparing the measured responses of the surrogate peptide to the responses of its stable isotope-labeled analogue that is added as an internal standard to the individual's sample.

In an embodiment, the measured response is the peak area ratio for a MS/MS transition characteristic of at least one fragment ion generated from the allele specific surrogate peptide. Additionally and/or alternatively, the measured response may be the peak area ratio for a MS/MS transition characteristic of at least one fragment ion generated from the common surrogate peptide. For example, in an embodiment, fragment ions are produced for each of the peptides during MS/MS. Where the fragment ion is from the C-terminus, the fragment ion may be denoted "y". Where the fragment ion is from the N-terminus, the fragment ion may be denoted "b". Additionally, the fragment ion may be identified by the number of amino acid residues. For example, for a peptide having the sequence LNILNNNYK (SEQ ID NO. 4), the fragment ion y4 would have the sequence NNYK (SEQ ID NO. 13). In an embodiment, the results may be reported as the peak area ratio (PAR) for the light (unlabeled) peptide (e.g., after trypsin digestion of the protein) to the PAR for the heavy (stable isotope labeled) peptide. This can provide a normalized response for the unlabeled tryptic peptide.

The method may be applied to any protein. In an embodiment, the protein is ApoL1. For example, for ApoL1, the allele specific surrogate peptide may have the amino acid sequence LNILNNNYK (SEQ ID NO. 4) derived from the wild-type allele (SEQ ID NO. 1), or may have the amino acid sequence LNMLNNNYK (SEQ ID NO. 5) derived from the G1 allele (SEQ ID NO. 2), or may have the amino acid sequence LNILNNK (SEQ ID NO. 6) derived from the G2 allele (SEQ ID NO. 3). Also for ApoL1, the common surrogate peptide may have the amino acid sequence of SETAEELK (SEQ ID NO. 7) and/or VAQELEEK (SEQ ID NO. 8) wherein the common surrogate peptide is present in each of the wild-type, G1 or G2 alleles. For the measurement of these peptides, the mass spectrometry may measure at least one of the transitions in Table 3. Also, for ApoL1, the presence or absence of the at least one allele specific surrogate peptide may be determined by comparing a measured response for the at least one allele specific surrogate peptide to a measured response for a stable isotope-labeled analogue listed in Table 2 of the at least one allele specific surrogate peptide.

As disclosed herein, a variety of body fluids from a subject may contain a protein variant coded by the gene allele of interest. In some cases, the body fluid is dried plasma or dried red blood cells, which are produced by addition of blood to a substrate that immobilizes red blood allowing for separation of the plasma. In some embodiments, the biological sample is dried blood, dried urine, or dried saliva collected on a suitable substrate.

Also disclosed are systems for performing the proteomic methods disclosed herein. For example, disclosed is a system for determining the genotype of a gene of interest in a subject, the system comprising: a device for providing a dried body fluid comprising a protein derived from the gene of interest; a station for subjecting the dried body fluid to digestion to generate at least one allele specific surrogate peptide and optionally, at least one common surrogate peptide for the protein; optionally, a station for chromatographic purification of the at least one allele specific surrogate peptide and the optional at least one stable isotope-labeled analogue of the at least one common surrogate peptide; and a station for analyzing the at least one allele specific surrogate peptide by mass spectrometry to determine the presence or amount of the at least one allele specific surrogate peptide in the biological sample.

In an embodiment, the device for providing a dried bodily fluid comprises a device to immobilize and separate red blood cells from plasma on a substrate. Also, in an embodiment, the system may further comprise a station for adding a stable isotope labeled internal standard for the at least one allele specific surrogate peptide and optionally, the at least one common surrogate peptide for the protein. Also, in some cases the station for mass spectrometry comprises a tandem mass spectrometer and/or the station for chromatography comprises high performance liquid chromatography (HPLC). The system may be high-throughput in nature. Also, in some cases, at least one of the stations is controlled by a computer.

BRIEF DESCRIPTION OF THE DRAWINGS

Having thus described the invention in general terms, reference will now be made to the non-limiting accompanying drawings, which are not necessarily drawn to scale.

FIG. 1 shows the amino acid sequence of ApoL1 wild-type (SEQ ID NO. 1), G1 (SEQ ID NO. 2), and G2 (SEQ ID NO. 3) protein variants, as well as the allele specific surrogate peptides produced by trypsin digestion of each protein variant in accordance with an embodiment of the disclosure. The wild-type (WT) specific surrogate peptide is LNILNNNYK (SEQ ID NO. 4). The G1 specific surrogate peptide is LNMLNNNYK (SEQ ID NO. 5). The G2 specific surrogate peptide is LNILNNK (SEQ ID NO. 6).

FIG. 2 shows certain ApoL1 common surrogate peptides produced by trypsin digestion of the WT, G1 and G2 variants in accordance with an embodiment of the disclosure. Qualifying peptide 1 is SETAEELK (SEQ ID NO. 7). Qualifying peptide 2 is VAQELEEK (SEQ ID NO. 8).

Figure 3:
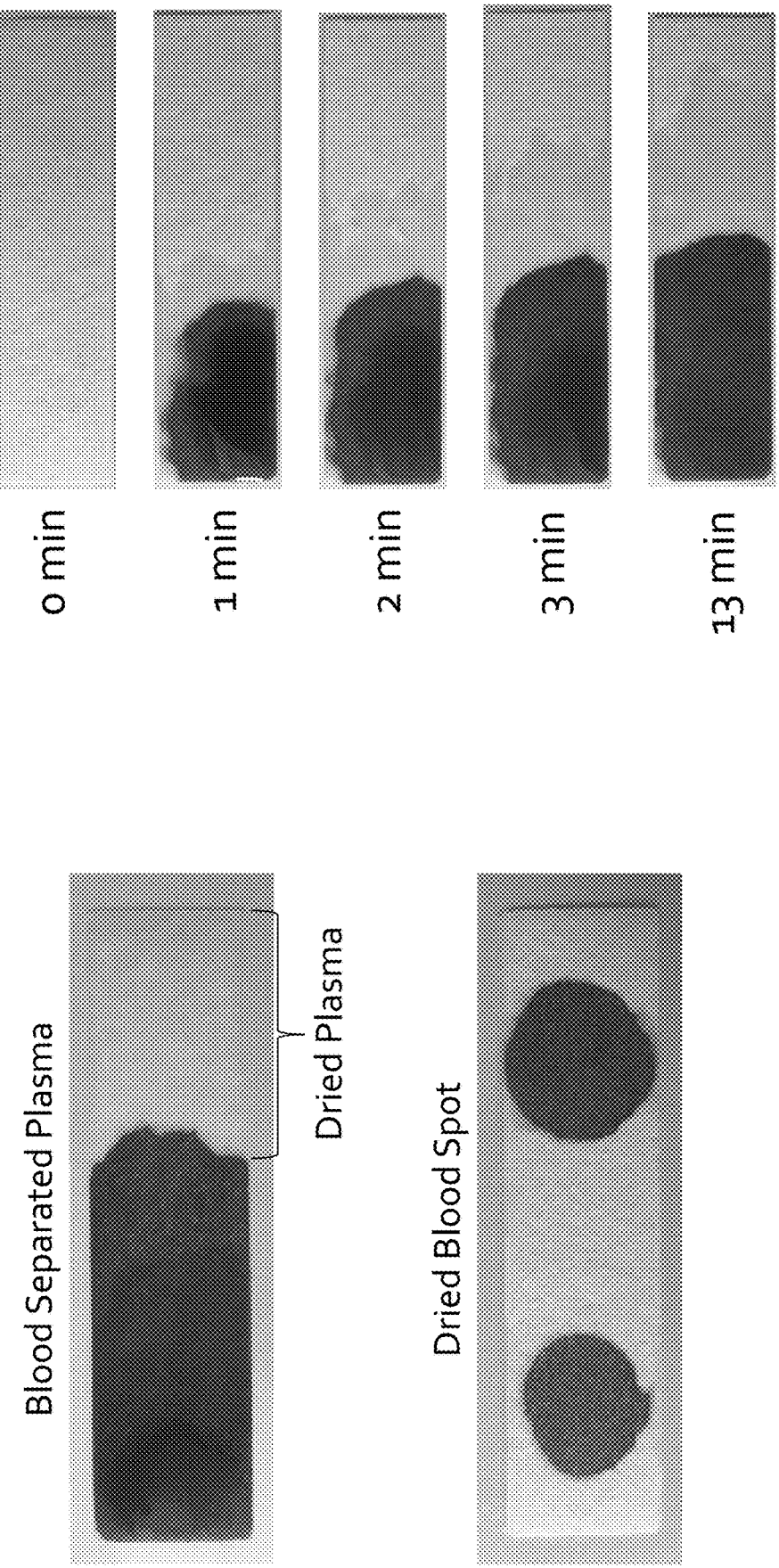

FIG. 3 shows certain methods for separation and drying of red blood cells and plasma from deposition of whole blood onto a laminar flow paper substrate to produce dried plasma, as well as time course for collection and drying of whole blood (i.e. dried blood spots) in accordance with an embodiment of the disclosure.

Figure 4:
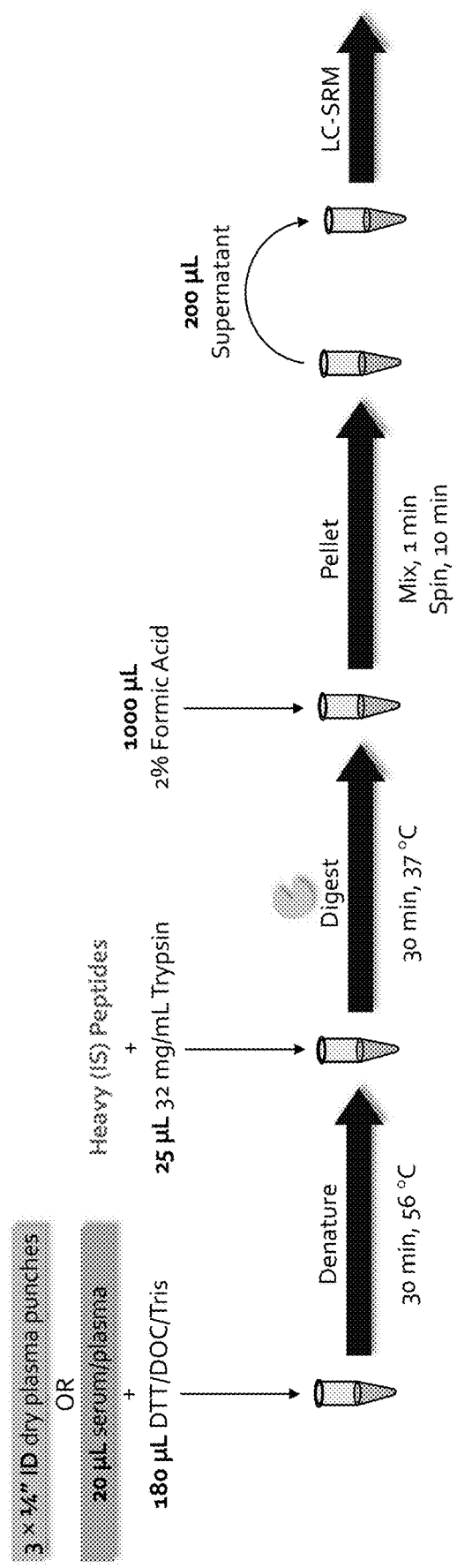

FIG. 4 shows a method for the determination of ApoL1 genotype in accordance with an embodiment of the disclosure.

Figure 5:
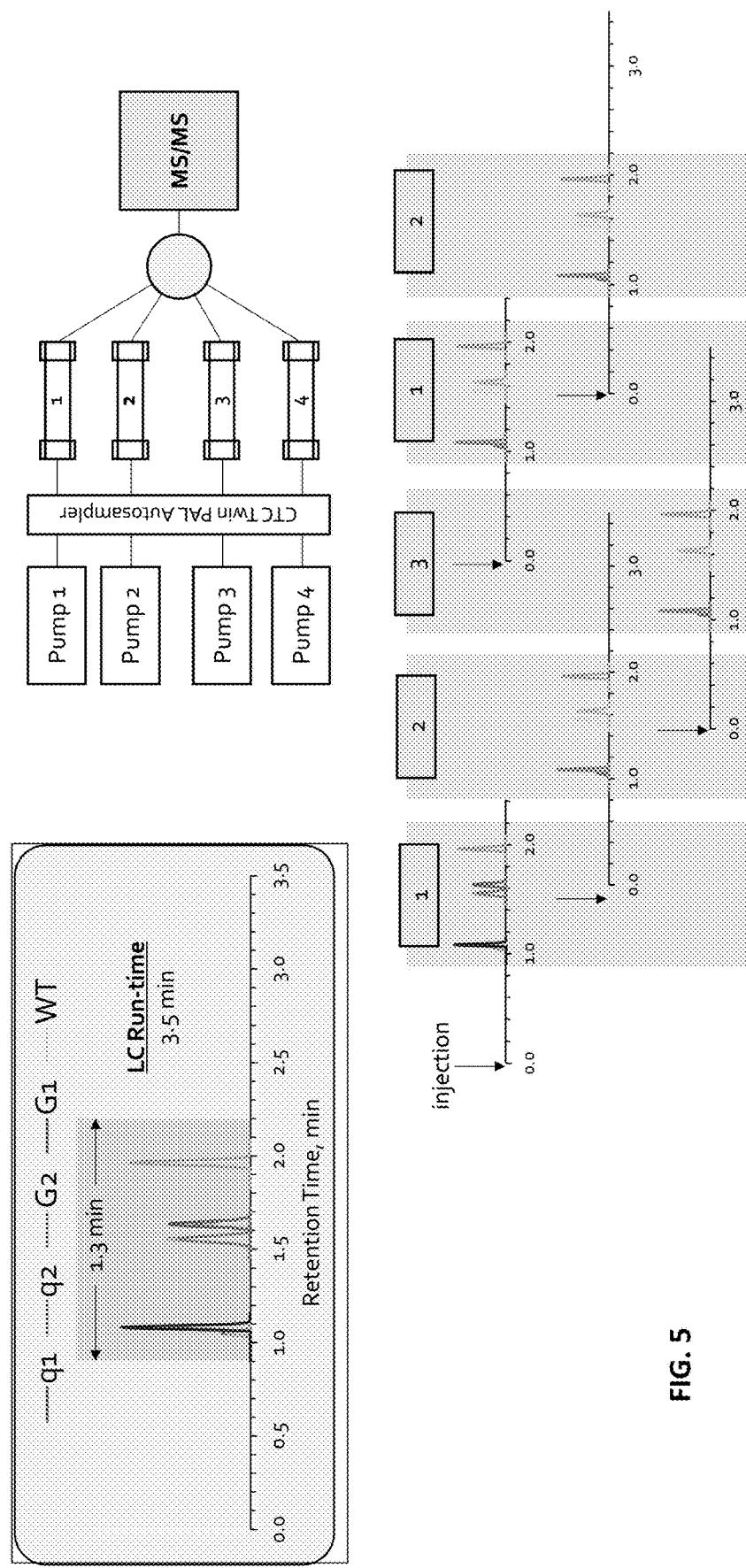

FIG. 5 shows a system for high-throughput proteomic genotyping in accordance with an embodiment of the disclosure.

FIG. 6 shows surrogate peptide detection patterns for ApoL1 alleles in accordance with an embodiment of the disclosure, where circles indicate positives and diamonds or empty boxes indicate negatives.

Figure 7:
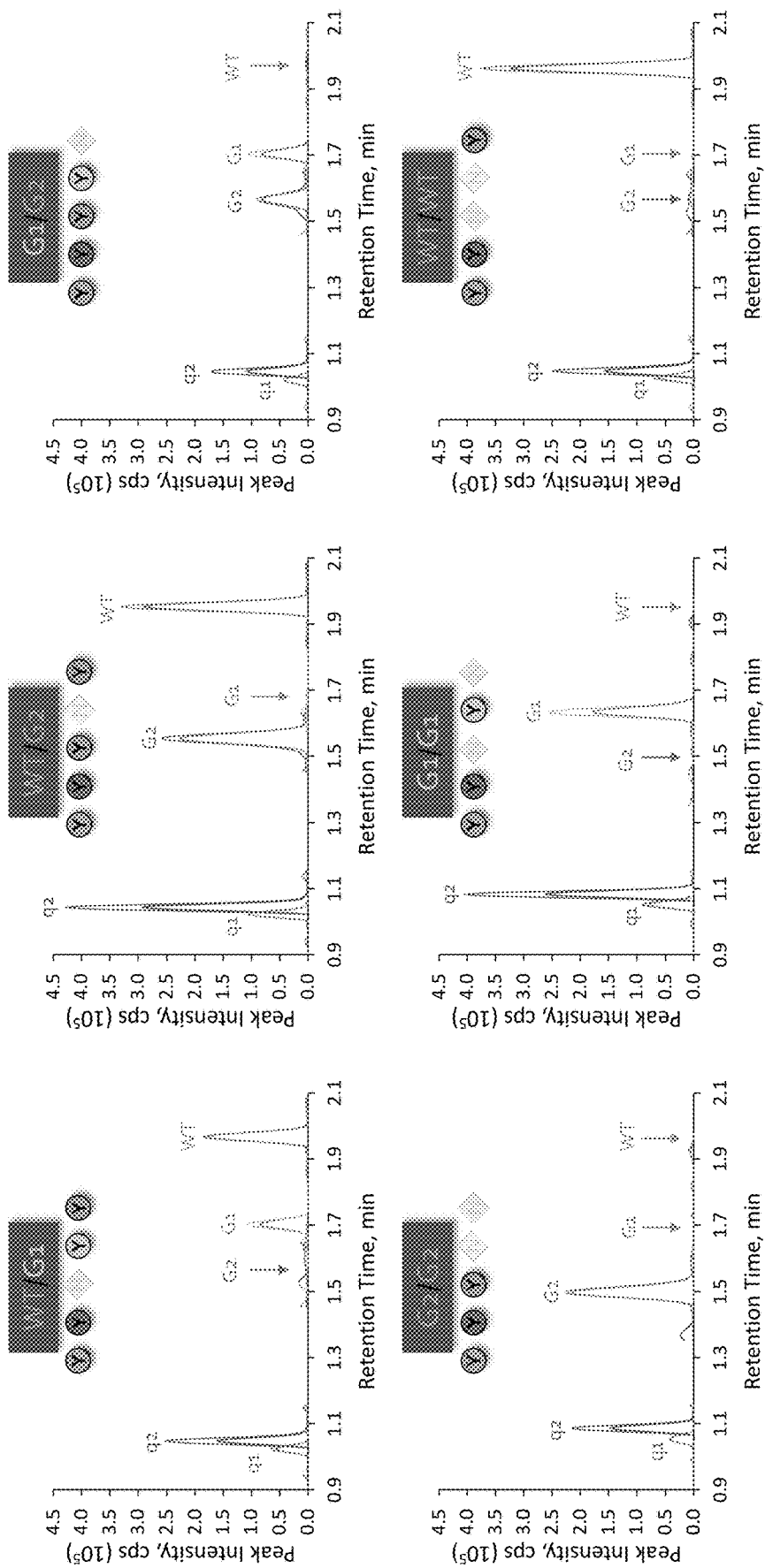
Figure 8:
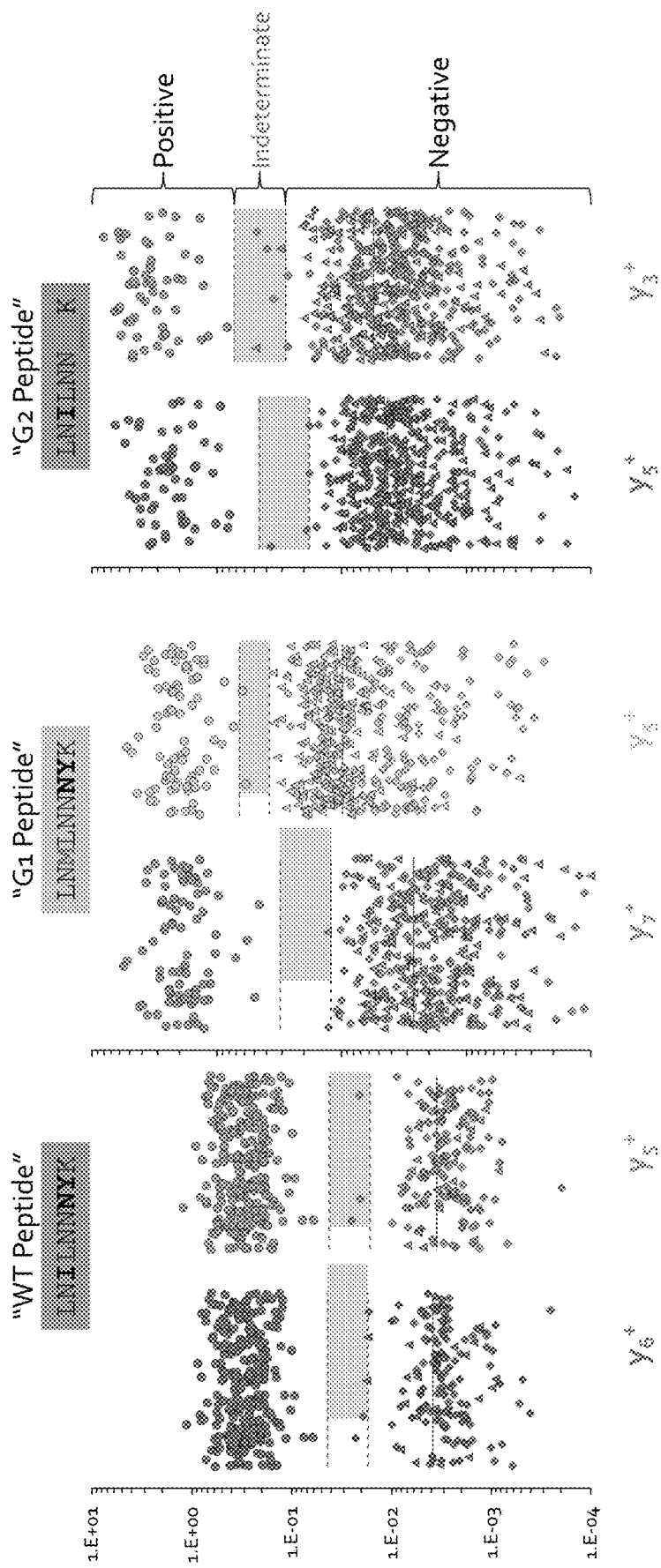

FIG. 7 shows a qualitative assignment of ApoL1 genotypes in accordance with an embodiment of the disclosure, where circles indicate positives and diamonds or empty boxes indicate negatives. In the figure, q1 and q2 represent the qualifying peptides FIG. 8 shows a semi-quantitative assessment of ApoL1 genotypes in accordance with an embodiment of the disclosure.

FIG. 9 shows a comparison of proteomic genotyping using dried plasma and liquid plasma as compared to Sanger DNA sequencing of blood.

Figure 10:
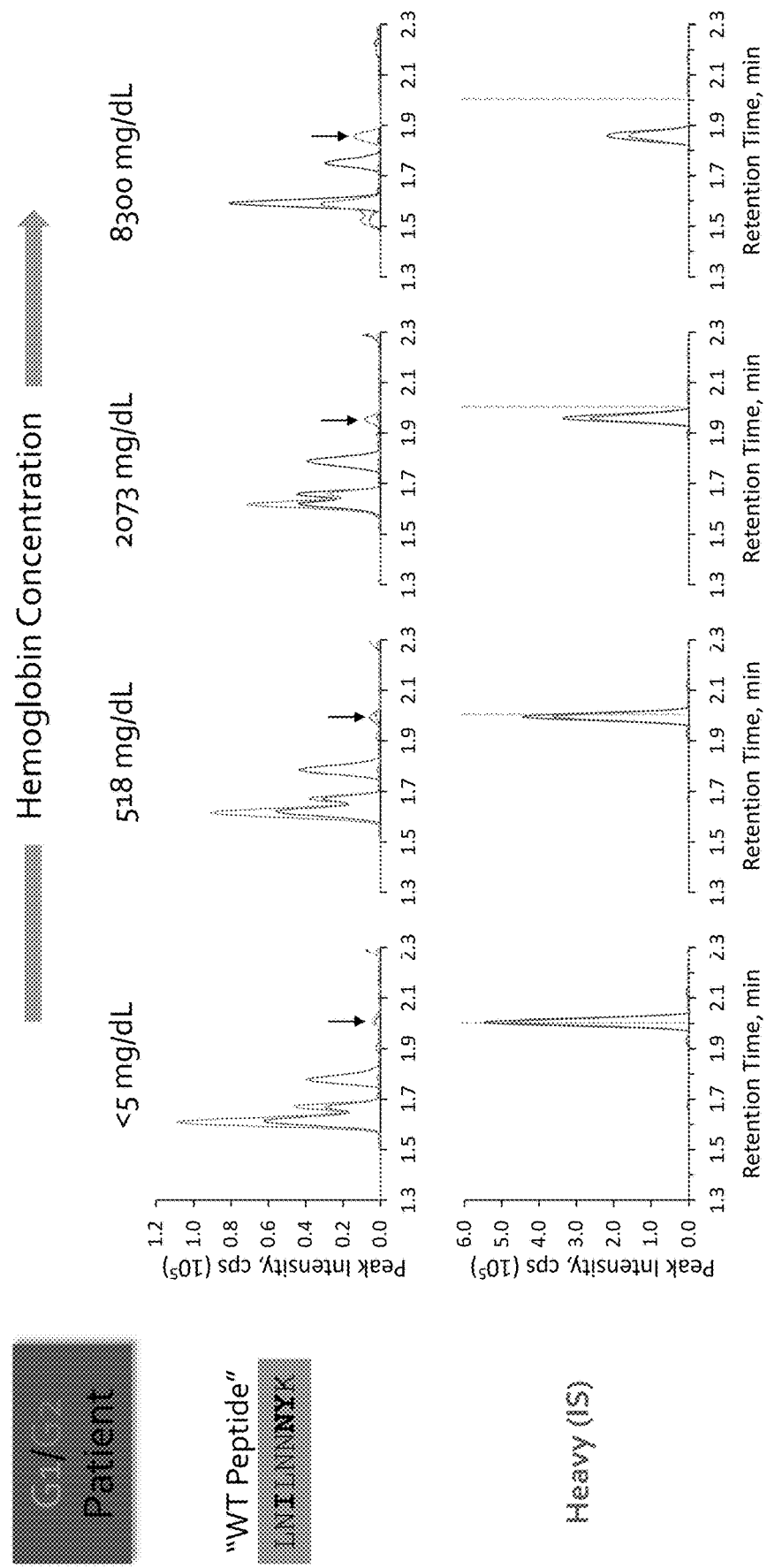

FIG. 10 shows an assessment of the ApoL1 wild-type (WT) peptide as a function of increasing hemoglobin concentration in accordance with an embodiment of the disclosure. Assessments were performed for samples having 5 mg/dL hemoglobin, 518 mg/dL hemoglobin, 2073 mg/dL hemoglobin and 8300 mg/dL hemoglobin as shown above the plots for both the wild-type (WT) peptide, and a heavy stable isotope internal standard (IS).

Figure 11:
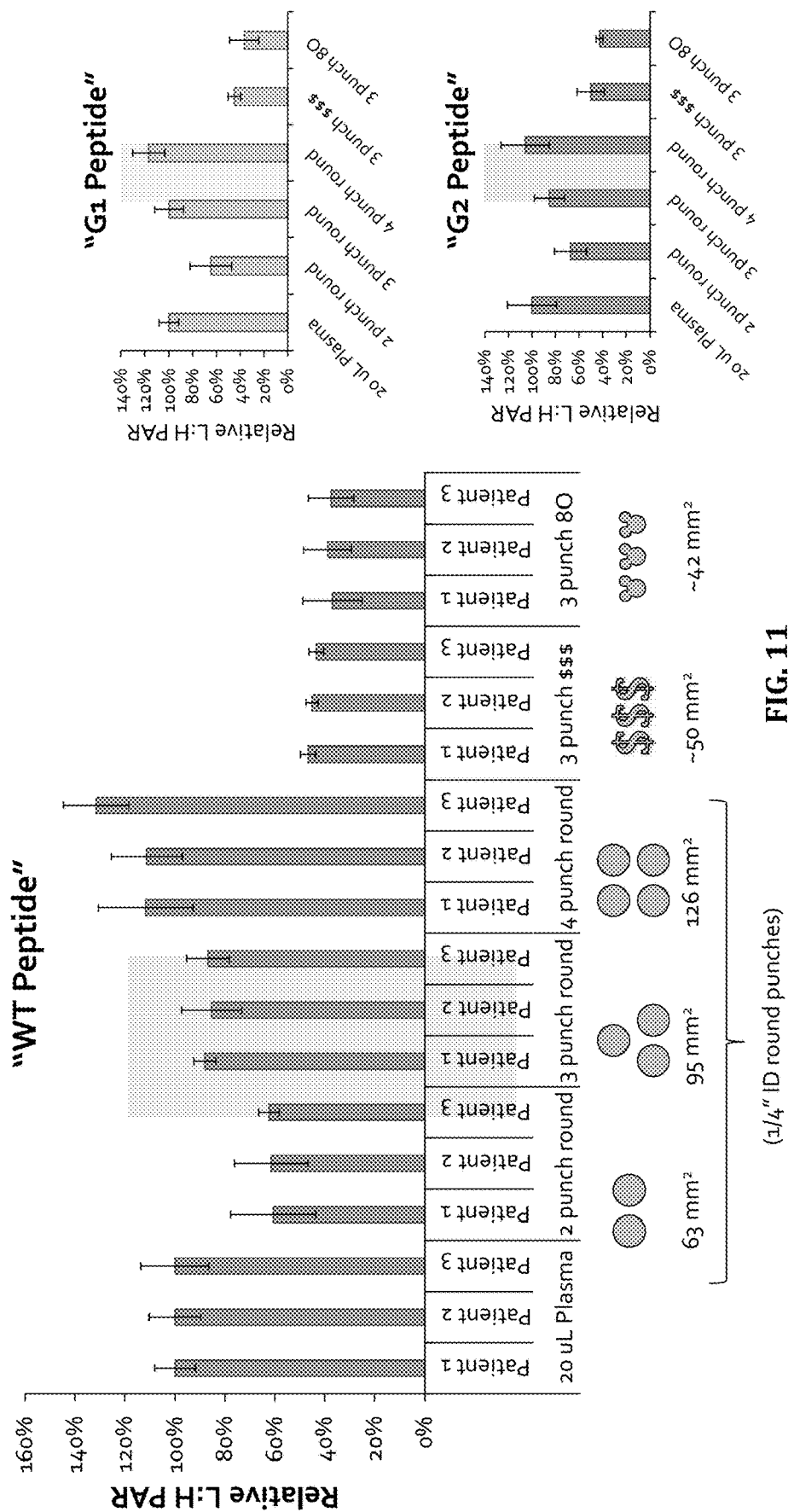

FIG. 11 shows a titration of ApoL1 WT, G1 and G2 peptides as a function of dried plasma immobilized on a laminar flow paper and harvested from ¼ inch punches in accordance with an embodiment of the disclosure. The x-axis indicates whether the sample was liquid plasma (20 uL), or dried plasma isolated using a solid substrate, where the approximate size and shape of the sampled substrate (i.e., "punches") is shown.

Figure 12:
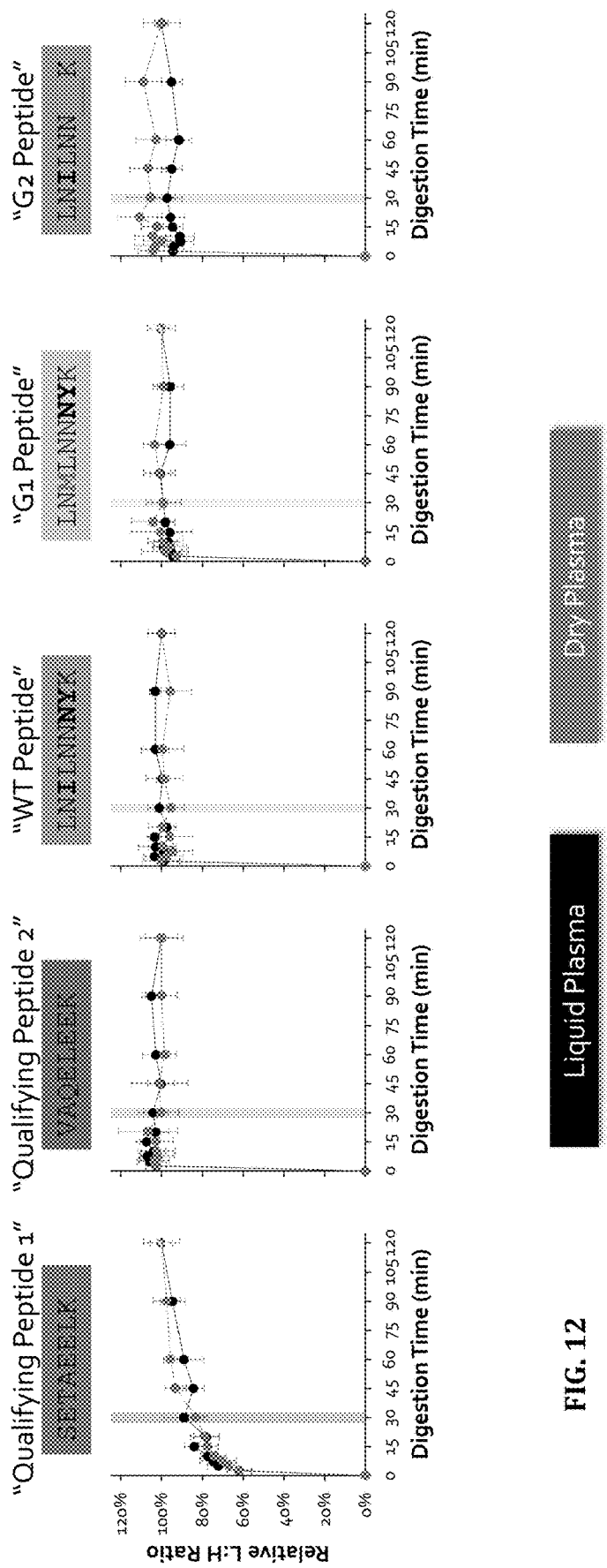

FIG. 12 shows a trypsin digestion time course to generate the qualifying peptides and the allele specific peptides using either liquid plasma (black circles) or dried plasma (gray circles) in accordance with an embodiment of the disclosure. The amount of digestion at the 30 min time point is indicated with the vertical shading.

Figure 13:
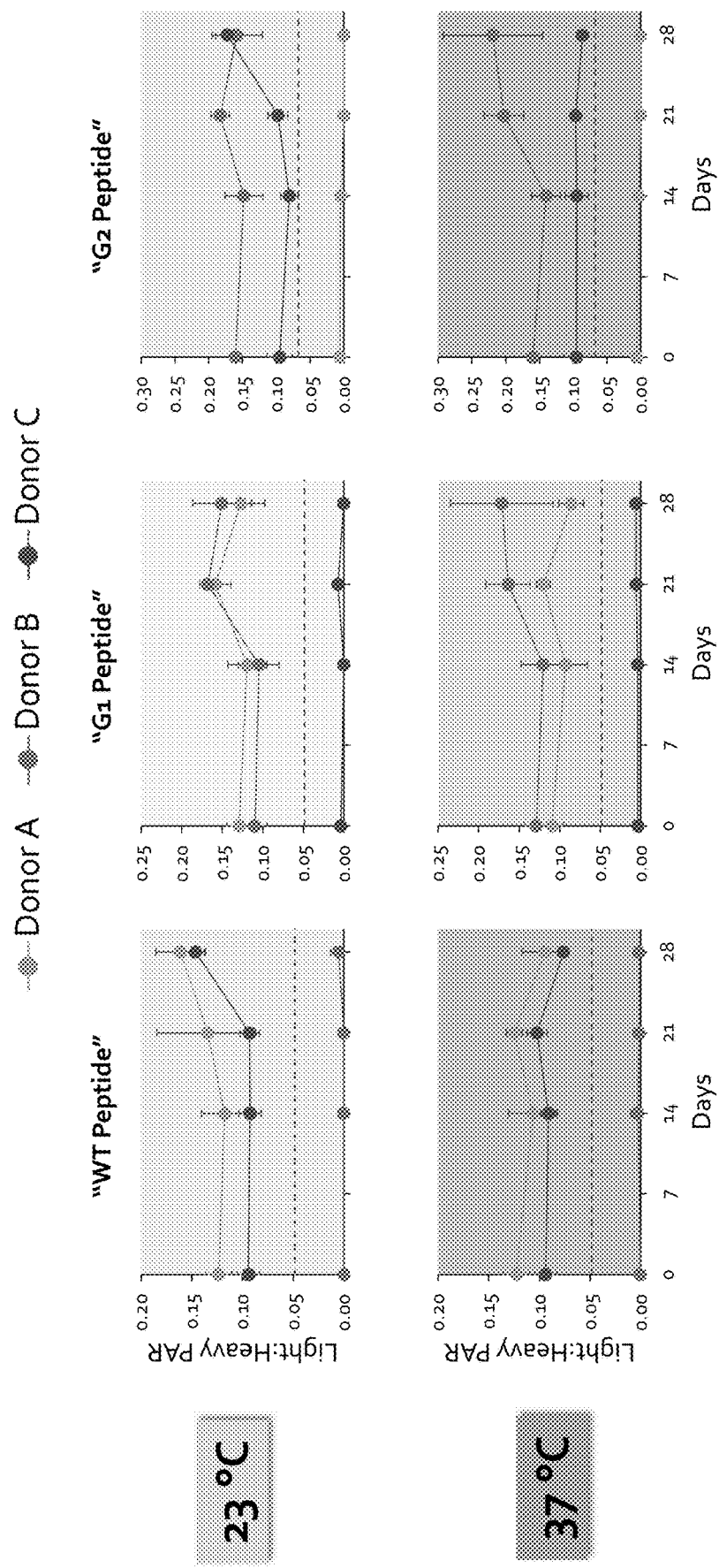

FIG. 13 shows stability of the wild-type and allele specific surrogate peptides in dry plasma stored at either 23° C. or 37° C. for up to 28 days in accordance with an embodiment of the disclosure.

Figure 14:
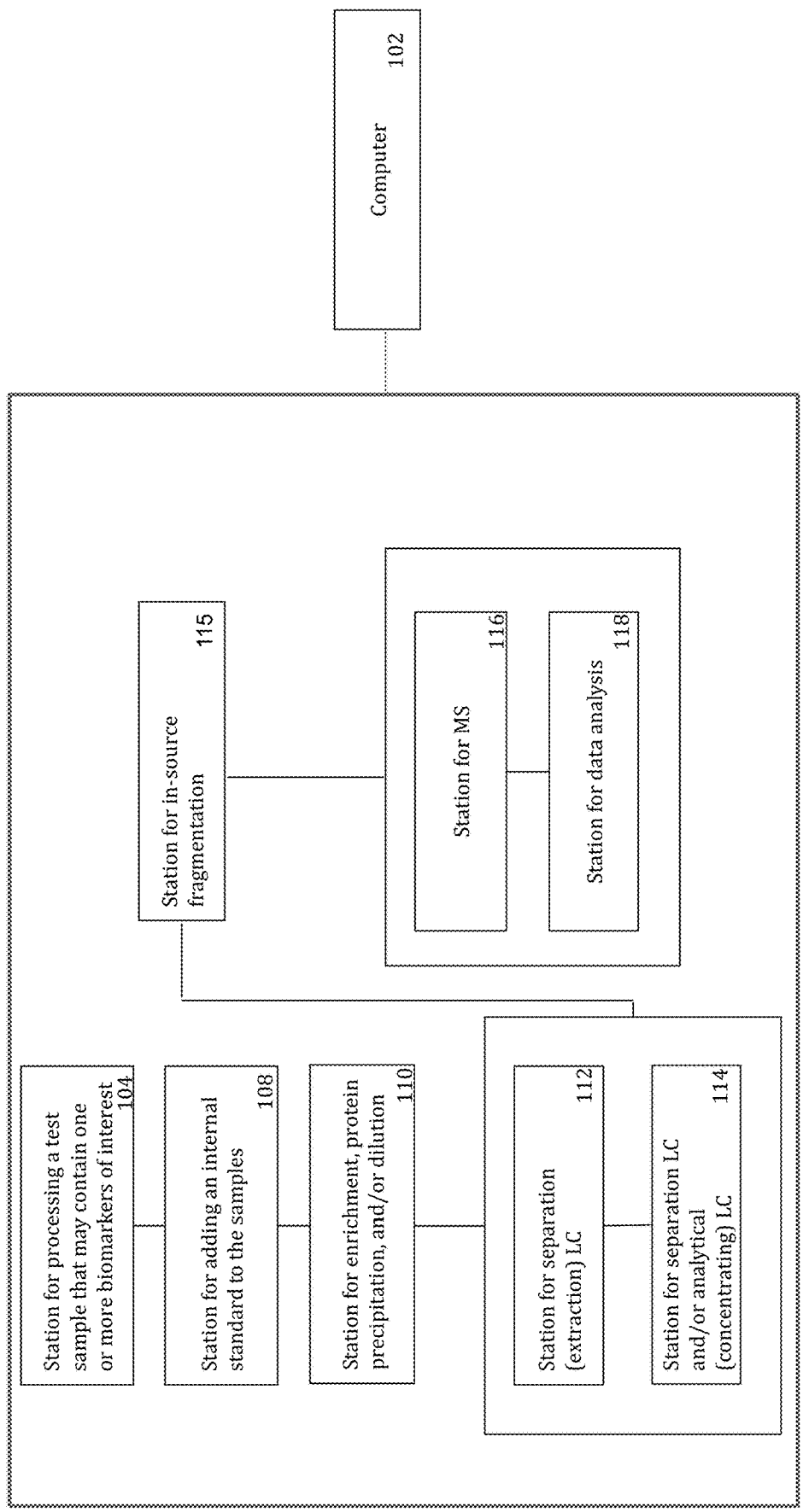

FIG. 14 shows a system for proteomic genotyping by LC-MS/MS in accordance with an embodiment of the disclosure.

DETAILED DESCRIPTION

The presently disclosed subject matter now will be described more fully hereinafter with reference to the accompanying description and drawings, in which some, but not all embodiments of the presently disclosed subject matter are shown. The presently disclosed subject matter can be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation. The disclosure utilizes the abbreviations shown below.

Abbreviations

APCI=atmospheric pressure chemical ionization
CV=Coefficient of variance
EDTA=Ethylenediaminotetraacetic acid
HTLC=high turbulence (throughput) liquid chromatography
HPLC=high performance liquid chromatography
IS=internal standard
LC=liquid chromatography
LLE=liquid-liquid extraction
LOB=limit of blank
LOQ=limits of quantification
LLOQ=lower limit of quantification
MS/MS=tandem mass spectrometry
N=number of replicates
N/A=not applicable
PAR=peak area ratio
QC=quality control
R=correlation coefficient Abbreviations SST=system suitability test
ULOQ=upper limit of quantification
2D-LC-MS/MS=two-dimensional liquid chromatography hyphenated to tandem mass spectrometry
(LC)-LC-MS/MS=two-dimensional liquid chromatography tandem hyphenated to mass spectrometry
(LC)-MS/MS=liquid chromatography hyphenated to tandem mass spectrometry Definitions While the following terms are believed to be well understood by one of ordinary skill in the art, the following definitions are set forth to facilitate explanation of the presently disclosed subject matter. Other definitions are found throughout the specification. Unless otherwise defined, all technical and scientific terms used herein have the same meaning as commonly understood by one of ordinary skill in the art to which this presently described subject matter belongs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

The terms "a", "an", and "the" refer to "one or more" when used in this application, including the claims. Thus, for example, reference to "a cell" includes a plurality of such cells, unless the context clearly is to the contrary (e.g., a plurality of cells), and so forth.

As used herein, the term "biomarker" or a "biomarker of interest" is any biomolecule that may provide biological information about the physiological state of an organism. In certain embodiments, the presence or absence of the biomarker may be informative. In other embodiments, the level of the biomarker may be informative. In an embodiment, the biomarker of interest may comprise a peptide, a hormone, a nucleic acid, a lipid or a protein. Or, other biomarkers may be measured. In an embodiment, the biomarker may comprise a peptide derived from ApoL1. In various embodiments the peptide may be a wild-type peptide, a G1 variant, or a G2 variant.

As used herein, the term "body fluid" refers to a liquid sample obtained from a biological source, including, but not limited to, an animal, a cell culture, an organ culture, and the like. Suitable samples include blood, plasma, serum, urine, saliva, tear, cerebrospinal fluid, or other liquid aspirate, all which are capable deposition onto a substrate for collection and drying. In an embodiment, the body fluid may be separated on the substrate prior to drying. For example, blood may be deposited onto a paper substrate and/or laminar flow device which limits migration of red blood cells allowing for separation of the blood plasma fraction prior to drying in order to produce a dried plasma sample for analysis.

As used herein, the terms "individual" and "subject" are used interchangeably. A subject may comprise an animal. Thus, in some embodiments, the biological sample is obtained from a mammalian animal, including, but not limited to a dog, a cat, a horse, a rat, a monkey, and the like. In some embodiments, the biological sample is obtained from a human subject. In some embodiments, the subject is a patient, that is, a living person presenting themselves in a clinical setting for diagnosis, prognosis, or treatment of a disease or condition.

As used herein, a subject may comprise an animal. Thus, in some embodiments, the biological sample is obtained from a mammalian animal, including, but not limited to a dog, a cat, a horse, a rat, a monkey, and the like. In some embodiments, the biological sample is obtained from a human subject. In some embodiments, the subject is a patient, that is, a living person presenting themselves in a clinical setting for diagnosis, prognosis, or treatment of a disease or condition.

As used herein, the terms "purify" or "separate" or derivations thereof do not necessarily refer to the removal of all materials other than the analyte(s) of interest from a sample matrix. Instead, in some embodiments, the terms "purify" or "separate" refer to a procedure that enriches the amount of one or more analytes of interest relative to one or more other components present in the sample matrix. In some embodiments, a "purification" or "separation" procedure can be used to remove one or more components of a sample that could interfere with the detection of the biomarker of interest, for example, one or more components that could interfere with detection of an analyte by mass spectrometry.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

The chromatographic column typically includes a medium (i.e., a packing material) to facilitate separation of chemical moieties (i.e., fractionation). The medium may include minute particles. The particles may include a bonded surface that interacts with the various chemical moieties to facilitate separation of the chemical moieties such as the biomarker analytes quantified in the experiments herein. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column may include an inlet port for receiving a sample and an outlet port for discharging an effluent that includes the fractionated sample. In the method, the sample (or prepurified sample) may be applied to the column at the inlet port, eluted with a solvent or solvent mixture, and discharged at the outlet port. Different solvent modes may be selected for eluting different analytes of interest. For example, liquid chromatography may be performed using a gradient mode, an isocratic mode, or a polytyptic (i.e. mixed) mode. In one embodiment, HPLC may performed on a multiplexed analytical HPLC system with a C18 solid phase using isocratic separation with water:methanol as the mobile phase.

As used herein, the term "analytical column" refers to a chromatography column having sufficient chromatographic plates to effect a separation of the components of a test sample matrix. Preferably, the components eluted from the analytical column are separated in such a way to allow the presence or amount of an analyte(s) of interest to be determined. In some embodiments, the analytical column comprises particles having an average diameter of about 5 µm. In some embodiments, the analytical column is a functionalized silica or polymer-silica hybrid, or a polymeric particle or monolithic silica stationary phase, such as a phenyl-hexyl functionalized analytical column.

Analytical columns can be distinguished from "extraction columns," which typically are used to separate or extract retained materials from non-retained materials to obtained a "purified" sample for further purification or analysis. In some embodiments, the extraction column is a functionalized silica or polymer-silica hybrid or polymeric particle or monolithic silica stationary phase, such as a Poroshell SBC-18 column.

The term "heart-cutting" refers to the selection of a region of interest in a chromatogram and subjecting the analytes eluting within that region of interest to a second separation, e.g., a separation in a second dimension.

The term "matrix-assisted laser desorption ionization," or "MALDI" as used herein refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization," or "ESI," as used herein refers to methods in which a solution is passed along a short length of capillary tube, to the end of which is applied a high positive or negative electric potential. Upon reaching the end of the tube, the solution may be vaporized (nebulized) into a jet or spray of very small droplets of solution in solvent vapor. This mist of droplet can flow through an evaporation chamber which is heated slightly to prevent condensation and to evaporate solvent. As the droplets get smaller the electrical surface charge density increases until such time that the natural repulsion between like charges causes ions as well as neutral molecules to be released.

The term "ionization" and "ionizing" as used herein refers to the process of generating an analyte ion having a net electrical charge equal to one or more electron units. Negative ions are those ions having a net negative charge of one or more electron units, while positive ions are those ions having a net positive charge of one or more electron units.

The term "desorption" as used herein refers to the removal of an analyte from a surface and/or the entry of an analyte into a gaseous phase.

As used herein, the term "hemolysed" refers to the rupturing of the red blood cell membrane, which results in the release of hemoglobin and other cellular contents into the plasma or serum and the term "lipemic" refers to an excess of fats or lipids in blood.

As used herein, "liquid plasma" is plasma that is obtained from drawing blood from a patient and that is separated from the red blood cells but that remains in a liquid state. Liquid plasma is generally obtained from subjects by phlebotomy or venipuncture.

As used herein, "dried plasma" is plasma that has been allowed to dry. Dried plasma may be produced following separation from red blood cells by migration of the plasma through pores of a solid substrate (e.g., by laminar flow) which restrict migration of cells as is described in more detail herein.

As used herein, a "sampling paper" or "filter" or "filter membrane" or "laminar flow paper" or "laminar flow device" are terms used interchangeably to refer to a solid substrate for the collection of dried blood and plasma may comprise a filter paper or membrane onto which blood can be spotted and that allows for the migration of the plasma away from the red blood cells to produce a region that is substantially plasma and that upon drying, provides a sample of dried plasma.

As used herein, a "genotype" is the DNA sequence of the two alleles present in a gene that may encode a protein sequence.

As used herein a "surrogate peptide" is a peptide derived from a protein and that provides sequence information about the protein. As used herein, the terms "variant specific surrogate peptide" and/or "allele specific surrogate peptide" and/or "genotype specific surrogate peptide" is a peptide derived from a protein and that has a unique amino acid sequence directly attributable to the DNA sequence of the gene that encodes for the protein. Determination of the sequence of the allele specific surrogate peptide can be used to infer the genotype of at least one allele of the gene. Thus, as used herein, an "allele specific surrogate peptide" is a peptide that provides sequence information about the allele which encodes the protein. For example, for ApoL1, a wild-type surrogate peptide indicates that the protein is derived from a wild-type allele, whereas a G1 surrogate peptide indicates that the protein is derived from the G1 allele, and a G2 surrogate peptide indicates that the protein is derived from the G2 allele.

As used herein, a "common surrogate" peptide or "qualifying peptide" or 'qualifying surrogate peptide" is a peptide that has a unique amino acid sequence that does not vary when the DNA sequence at a locus of interest may vary. Thus, as used herein, a "common surrogate peptide" or "qualifying peptide" comprises a peptide sequence that is common to the wild-type allele as well as all of the alleles being interrogated. Determination of the sequence of the common surrogate peptide will not vary with changes in the genotype at the locus of interest, and thus can be used as internal controls to differentiate a true negative signal from a sample processing error.

As used herein, a "protein variant" is a protein that has an amino acid sequence that is different from the most common or wild-type sequence.

As used herein, a "proteomic profile" is a profile of surrogate peptides that can be used to determine the genotype of an individual at a locus of interest.

Analysis of APOL1 Genotypes by LC-MS/MS

Thus, embodiments of the present invention relate to methods and systems for proteomic analysis of genotypes. The present invention may be embodied in a variety of ways.

Methods for Analysis of Allele specific Proteomic Profiles by LC-MS/MS

In one embodiment, the present invention comprises a method for determining the genotype of a subject, the method comprising: providing a body fluid onto a substrate and drying; subjecting the dry body fluid to digestion to produce allele specific surrogate peptides from the protein variant contained therein; using mass spectrometry to detect allele specific surrogate peptides present in the sample; and determining the genotype based on the proteomic profile of the allele specific surrogate peptides. Thus, in an embodiment, provided is a method for determining a genotype of a gene of interest in a subject, the method comprising: providing a body fluid from the subject, the bodily fluid containing a protein derived from the gene of interest; depositing the body fluid on a solid substrate, wherein the fluid is allowed to dry to produce a dry specimen; digesting the dry specimen to generate at least one allele specific surrogate peptide for the protein; using mass spectrometry to detect the at least one allele specific surrogate peptide present in the digested sample; and determining the genotype of the subject based on the presence or absence or amount of the at least one allele specific surrogate peptide. In an embodiment, the method may further comprise measuring the amount of at least one common surrogate peptide that is common to each genotype of the gene of interest. Also, in an embodiment, the at least one allele specific surrogate peptide is analyzed by liquid chromatography tandem mass spectrometry (LC-MS/MS). In certain embodiments, the method may further comprise measuring the amount of the protein variant(s) coded by the gene alleles of interest by detection of the allele specific surrogate peptides. In certain embodiments, the method may further comprise detecting the presence of at least one common surrogate peptide that is common to all protein variants coded by the alleles of the gene of interest. Thus, in certain embodiments, the protease digestion may produce common surrogate peptides (or qualifying peptides) that are common to the various alleles present for the gene. In an embodiment, the presence or absence of the at least one allele-specific surrogate peptide is determined by comparing a measured response for at least one allele-specific surrogate peptide to a measured response for at least one common surrogate peptide.

In some embodiments, digestion is performed with the protease trypsin. Or, other proteases and chemicals can be used for protein hydrolysis. Also, in some embodiments, the protein derived from the gene of interest is denatured prior to digestion to facilitate digestion.

In some cases an internal standard(s) may be used. The internal standard may, in some embodiments, be added prior to the step of digestion. For example, the presence or absence of the at least one allele specific surrogate peptide may be determined by comparing a measured response for the at least one allele specific surrogate peptide to a measured response for a stable isotope-labeled analogue of the at least one allele specific surrogate peptide that is added to the sample. Additionally and/or alternatively, the presence or absence of the at least one common surrogate peptide may be determined by comparing a measured response for the common surrogate peptide to the response for a stable isotope-labeled common surrogate peptide.

In an embodiment, fragment ions are produced for each of the peptides during MS/MS. Where the fragment ion is from the C-terminus, the fragment ion may be denoted "y". Where the fragment ion is from the N-terminus, the fragment ion may be denoted "b". Additionally, the fragment ion may be identified by the number of amino acid residues. For example, for a peptide having the sequence LNILNNNYK (SEQ ID NO. 4), the fragment ion y4 would have the sequence NNYK (SEQ ID NO. 13). In an embodiment, the results may be reported as the peak area ratio (PAR) for the light (unlabeled) peptide (e.g., after trypsin digestion of the protein) to the PAR for the heavy (stable isotope labeled) peptide. This can provide a normalized response for the unlabeled tryptic peptide.

The method may be applied to any protein. In an embodiment, the protein is ApoL1. For example, for ApoL1, the allele specific surrogate peptide may have the amino acid sequence LNILNNNYK (SEQ ID NO. 4) derived from the wild-type allele (SEQ ID NO. 1), or may have the amino acid sequence LNMLNNNYK (SEQ ID NO. 5) derived from the G1 allele (SEQ ID NO. 2), or may have the amino acid sequence LNILNNK (SEQ ID NO. 6) derived from the G2 allele (SEQ ID NO. 3). Also for ApoL1, the common surrogate peptide may have the amino acid sequence of SETAEELK (SEQ ID NO. 7) and/or VAQELEEK (SEQ ID NO. 8) wherein the common surrogate peptide is present in each of the wild-type, G1 or G2 alleles. For the measurement of these peptides, the mass spectrometry may measure at least one of the transitions in Table 3. Also, for ApoL1, the presence or absence of the at least one allele specific surrogate peptide may be determined by comparing a measured response for the at least one allele specific surrogate peptide to a measured response for a stable isotope-labeled analogue listed in Table 2 of the at least one allele specific surrogate peptide.

As disclosed herein, a variety of body fluids may be used. In some cases, the body fluid may be plasma or blood. In some embodiments, the body fluid may be used to produce dried plasma. Or, the bodily fluid may comprise at least one of dried blood, dried urine or dried saliva.

Also, in some embodiments, the sample may be subjected to a purification step prior to ionization for mass spectrometry. The purification step may comprise chromatography. As discussed herein, in certain embodiments, the chromatography comprises high performance liquid chromatography (HPLC). The LC step may comprise one LC separation, or multiple LC separations. In one embodiment, the chromatographic separation comprises extraction and analytical liquid chromatography. Additionally or alternatively, high turbulence liquid chromatography (HTLC) (also known as high throughput liquid chromatography) may be used.

The purification may comprise steps in addition to HPLC or other types of chromatographic separation techniques. In alternate embodiments, the method may comprise at least one of liquid-liquid extraction, supported liquid extraction or dilution. In one embodiment, the sample is diluted into a solvent or solvent mixture that may be used for LC and/or MS (e.g., LC-MS/MS or 2D-LC-MS/MS).

As a non-limiting example, the methods of the disclosure have been applied to the proteomic analysis of ApoL1 genotypes. The wild-type (WT) allele and risk variant alleles (G1 and G2) code for ApoL1 which have unique amino acid sequences at position 384 or 388-389 (FIG. 1). Upon tryptic digestion of ApoL1 (e.g., FIGS. 1 and 2), each variant form consequently produces a distinct proteolytic peptide derived from residues 382 to 390 (or 382 to 388 in the case of the G2 deletion), which can be detected by LC-MS/MS as a surrogate for presence of the corresponding ApoL1 variant (FIG. 6 and FIG. 7). Thus, using the systems and method disclosed herein, the three genetic variants of ApoL1—wild-type (WT), G1, and G2—may be determined by identifying the corresponding mutations in the protein sequence of ApoL1 circulating in whole blood by analysis of a dried blood or dried blood fraction (FIG. 3).

FIG. 3 shows a substrate having zones of dried red blood cells and dried plasma isolated using a plasma separator strip compared to a paper having a dried blood spot, but that does not have the plasma separated from the blood (see FIG. 3 left panel, top and bottom, respectively). The right side of FIG. 3 shows the extent of separation with time. Although dried blood spots are commonly used specimens in clinical analyses, the analysis may suffer from interferences derived from red blood cells (e.g., hemoglobin). Laminar flow paper may be used to separate the plasma fraction of blood deposited from the cellular components due to differential migration of the plasma and cells through the paper, resulting in a cell-free plasma fraction that can be dried and assayed.

The identification of the surrogate peptide(s) may be accomplished by first denaturing the dried blood fraction (i.e., dried plasma), followed by trypsin digestion to produce proteolytic surrogate peptides specific to the three variant forms of ApoL1 (FIG. 4). The digested plasma may then directly analyzed by LC-MS/MS to determine the presence or absence of the respective surrogate peptides to infer the presence or absence of the associated ApoL1 variant (FIG. 4 and FIG. 5).

Two common surrogate peptides (i.e., qualifying peptides) that are common among all three (i.e., WT, G1 and G2) ApoL1 variants can also be monitored for qualifying sample processing (FIG. 2). For example, it is possible another as of yet unknown ApoL1 variant may exist that codes for a different amino acid mutation between residues 382 or 390. If an individual is homozygous for this mutation (or heterozygous for two such unknown mutations), this would result in no detectable variant-specific surrogate peptide. In order to differentiate this from a sample processing error, two additional surrogate peptides produced by trypsin digestion that neighbor the variant-specific surrogate peptide are monitored, which should be detectable in all properly processed samples regardless of the ApoL1 variant. Thus, detection of one or more of these two "qualifying surrogate peptides" confirms proper sample processing, such that confident interpretation of the variant-specific surrogate peptide detection may follow without concern for the integrity of the processed specimen.

The presence or absence of the surrogate peptides (variant or qualifying) may be determined by comparing the measured responses of the surrogate peptide to the responses of its stable isotope-labeled analogue that is added as an internal standard to sample aliquots prior to trypsin digestion. Based on the pattern of surrogate peptides detected, the genotype of the specimen/individual can be determined.

FIG. 4 shows a method for the determination of ApoL1 genotype using dried plasma (3×¼" ID round punches from a paper substrate) (e.g., a sampling paper) in accordance with an embodiment of the disclosure. The sample (i.e., dried plasma) may be added to digestion buffer. After a short incubation at an elevated temperature (e.g., 30 min at 56° C.) to denature proteins present in the sample, trypsin and an internal standard may be added and digestion is allowed to proceed (e.g., 30 min at 37° C.). Next formic acid can be added to terminate the trypsin digestion and precipitate acid-insoluble materials (i.e., deoxycholate), and an aliquot of the supernatant added to the LC-MS/MS system.

The samples may then be analyzed by high-throughput LC-MS/MS. FIG. 5 shows a system for high-throughput proteomic genotyping. In one embodiment, the LC method parameters were optimized to ensure chromatographic resolution of isobaric interferences of each surrogate peptide, which resulted in an LC method having a total run-time of 3.5 minutes. When employed on a multiplexing LC system, such as the ARI Transcent™ TLX-4, injections may be run in parallel with injections staggered every 1.5 minutes to improve the duty cycle of the mass spectrometric analysis.

FIG. 6 shows surrogate peptide detection patterns for ApoL1 in accordance with an embodiment of the disclosure. Thus, a subject who is a homozygous wild-type (WT/WT) will have the WT peptide, as well as the two common peptides (SETAEELK (SEQ ID NO. 7) and VAQELEEK (SEQ ID NO. 8)). Similarly, a subject who is homozygous for either the G1 allele (G1/G1) or the G2 allele (G2/G2) will have the G1 or G2 peptide, respectively, as well as the two common peptides (SETAEELK (SEQ ID NO. 7) and VAQELEEK (SEQ ID NO. 8)). Subjects who are heterozygous for WT, G1 or G2 will exhibit the patterns shown (FIG. 6).

FIG. 7 shows a qualitative assignment of ApoL1 genotypes in accordance with an embodiment of the disclosure.

Shown are example chromatograms derived from individuals of all six potential genotypes. All five surrogate peptides are detected using two SRM transitions. When the ApoL1 variant is present in the individual, the corresponding variant-specific surrogate peptide is clearly visible/detected in the chromatogram. When the ApoL1 variant is absent in the individual, the corresponding variant specific surrogate peptide is clearly not visible/detected in the chromatogram. Notably, the two qualifying surrogate peptides are present in all six individuals regardless of genotype.

FIG. 8 shows a semi-quantitative assessment of ApoL1 genotypes in accordance with an embodiment of the disclosure. In this experiment, several hundred specimens and specimen pools were analyzed as liquid plasma and qualitatively assigned as negative (triangles/diamonds) or positive (circles) for a given variant-specific surrogate peptide based on visual interpretation of the corresponding chromatograms. Based on the normalized response for each transition shown on the y axis as a peak area ratio for fragments (e.g. $y_6+$ or $y_5+$ for the wild-type allele specific peptide) of the unlabeled allele specific peptide as compared to the heavy isotope labeled allele specific peptide (light: heavy peptide peak area ratio, PAR) measured in the associated negative specimens, the limit of detection was calculated as the mean normalized response, plus four (4) standard deviations, below which a sample would be classified as definitively negative. The threshold for definitive positive detection of the variant-specific surrogate peptide was calculated as the mean normalized response in the associated negative specimens, plus 12 standard deviations.

FIG. 9 shows a comparison of DNA sequencing and proteomic genotyping using dried plasma vs liquid plasma biological samples. Matched liquid and dry plasma specimens were obtained from 209 African American donors for proteomic analysis, along with whole blood for Sanger sequencing. Genotypes of each donor determined by Sanger sequencing was in perfect agreement with the genotypes assigned by proteomic analysis from both liquid and dry plasma specimens indicating that proteomic profiling is a viable option for LC-MS/MS/analysis of biomarkers of interest.

FIG. 10 shows an assessment of the ApoL1 wild-type (WT) peptide as a function of hemoglobin concentration in accordance with an embodiment of the disclosure. In some embodiments, hemoglobin may interfere with the detection of a biomarker of interest in two significant ways. First, at higher concentrations of hemoglobin an isobaric interferent was observed in one of two SRM transitions for the WT-surrogate peptide, which confounded interpretation of specimens with WT-negative genotypes (i.e., G1/G1, G2/G2 or G1/G2). Second, a matrix effect was observed which resulted in lower analytical response due to ion suppression.

FIG. 11 shows a titration of ApoL1 WT, G1 and G2 peptides as a function of dried plasma immobilized on a filter paper and harvested from ¼ inch punches in accordance with an embodiment of the disclosure. The cross-section and number of dry plasma punches required to provide equivalent analytical response to liquid plasma was evaluated to ensure equivalent assay performance from both liquid and dry plasma. Different cross-sections were considered to determine which was most practical for implementation in a 96-well plate format. Three individuals were evaluated with the following genotypes: WT/WT, WT/G1, and WT/G2. Relative to the liquid plasma, the relative response of each surrogate peptide was consistent across individuals and genotypes indicating response recovery in dry plasma was related solely to the total surface area analyzed. Based on these analyses, it was concluded that an equivalent analytical response of 20 uL liquid plasma could be obtained from between 96 and 126 $mm^2$ of dry plasma for the wild-type peptide (WT), as well as G1 and G2. The WT graph shows examples of other cut-out shapes that may be used. Signal is generally proportional to the amount of cut-out used per sample.

FIG. 12 shows a trypsin digestion time course using either liquid plasma or dried plasma in accordance with an embodiment of the disclosure. The formation of each surrogate peptide during digestion of liquid and dry plasm was evaluated in a time course analysis between 0 and 120 minutes. Samples of the liquid plasma digestion were collected at nine time points between 3 and 120 minutes. The profiles indicate digestion of each ApoL1 variant proceeds in a similar manner from both liquid and dry plasma specimens. Thus, there is virtually 100% digestion after about 2 hours.

FIG. 13 shows stability of protein variant measurements from dry plasma in accordance with an embodiment of the disclosure. It can be seen that the samples provide similar measured responses of the surrogate peptides even after 28 days at either 23 degrees Centigrade (the normal storage conditions) or 37 degrees Centigrade.

FIG. 14 shows a schematic ellustration of an embodiment of a system of the present invention.

Systems for LC-MS/MS Proteomic Genotyping

Other disclosed embodiments comprise systems. For example, disclosed is a system for determining the proteomic profile for genotype of interest in a subject, the system comprising: a device for providing a test sample comprising a protein or allele specific surrogate peptides derived from the genetic locus of interest; a station for subjecting the sample to protease digestion protease to generate the allele specific surrogate peptides; optionally, a station for chromatographic purification of the allele specific surrogate peptide(s); and a station for analyzing the allele specific surrogate peptide(s) by mass spectrometry to determine the presence or amount of the allele specific surrogate peptides in the biological sample. In an embodiment, disclosed is a system for determining the genotype of a gene of interest in a subject, the system comprising: a device for providing a dried body fluid comprising a protein derived from the gene of interest; a station for subjecting the dried body fluid to digestion to generate at least one allele specific surrogate peptide and optionally, at least one common surrogate peptide for the protein; optionally, a station for chromatographic purification of the at least one allele specific surrogate peptide; and a station for analyzing the at least one allele specific surrogate peptide by mass spectrometry to determine the presence or amount of the at least one allele specific surrogate peptide in the biological sample. In an embodiment, the protein is ApoL1.

In certain embodiments, the device for providing a biological sample may comprise a device to immobilize and separate red blood cells from plasma on a substrate. The system may further comprise a station for adding a stable isotope labeled internal standard for the at least one allele specific surrogate peptide and optionally, the at least one common surrogate peptide for the protein.

Also, as described in detail below, the station for mass spectrometry may comprise a tandem mass spectrometer. In an embodiment, the mass spectrometry is operated in Electrospray Ionization (ESI) mode.

Also, the station for chromatography may comprise various types of chromatography separately or used together such as, but not limited to, liquid-liquid chromatography, and/or high performance liquid chromatography (HPLC), and/or other types of chromatography described herein.

Also in certain embodiments, at least one of the stations is automated and/or controlled by a computer. For example, as described herein, in certain embodiments, at least some of the steps are automated such that little to no manual intervention is required.

In one embodiment, the station for chromatographic separation comprises at least one apparatus to perform liquid chromatography (LC). In one embodiment, the station for liquid chromatography comprises a column for extraction chromatography. Additionally or alternatively, the station for liquid chromatography comprises a column for analytical chromatography. In certain embodiments, the column for extraction chromatography and analytical chromatography comprise a single station or single column. For example, in one embodiment, liquid chromatography is used to purify the biomarker of interest from other components in the sample that co-purify with the biomarker of interest after extraction or dilution of the sample.

The system may also include a station for analyzing the chromatographically separated one or more biomarkers of interest by mass spectrometry to determine the presence or amount of the one or more biomarkers in the test sample. In certain embodiments, tandem mass spectrometry is used (MS/MS). For example, in certain embodiments, the station for tandem mass spectrometry comprises an Applied Biosystems API5500 or API6500 triple quadrupole or thermo Q-Exactive mass spectrometer.

The system may also comprise a station for partially purifying or denaturing peptides and/or proteins from the biological sample and/or diluting the sample. In an embodiment, the station for extraction comprises a station for immunoaffinity enrichment of the protein variant or resulting surrogate peptide. The station for immunoaffinity enrichment may comprise equipment and reagents for manipulation, washing, and stripping of the solid sorbent binding the immunoaffinity reagent. In some cases an isotopically-labeled internal standard is used to standardize losses of the biomarker that may occur during the procedures.

In certain embodiments, the methods and systems of the present invention may comprise multiple liquid chromatography steps. Thus, in certain embodiments, a two-dimensional liquid chromatography (LC) procedure is used. For example, in one embodiment, the method and systems of the present invention may comprise transferring the sample, or peptides derived from the sample, from a LC extraction column to an analytical column. In one embodiment, the transferring from the extraction column to an analytical column is done by a heart-cutting technique. In another embodiment, transfer from the extraction column to an analytical column by a chromatofocusing technique. Alternatively, transfer from the extraction column to an analytical column may be done by a column switching technique. These transfer steps may be done manually, or may be part of an on-line system.

Various columns comprising stationary phases and mobile phases that may be used for extraction or analytical liquid chromatography are described herein. The column used for extraction liquid chromatography may be varied depending on the biomarker of interest. In some embodiments, the extraction column is a functionalized silica or polymer-silica hybrid or polymeric particle or monolithic silica stationary phase, such as a Poroshell SBC-18 column. The column used for analytical liquid chromatography may be varied depending on the analyte and/or the column that was used for the extraction liquid chromatography step. For example, in certain embodiments, the analytical column comprises particles having an average diameter of about 5 μm.

As noted herein, in certain embodiments, the mass spectrometer may comprise a tandem mass spectrometer (MS/MS). For example, in one embodiment of the methods and systems of the present invention, the tandem mass spectrometry comprises a triple quadrupole tandem mass spectrometer. In other embodiments, the tandem mass spectrometer may be a hybrid mass spectrometer, such as a quadrupole-oribtrap or a quadrupole-time-of-flight mass spectrometer.

The tandem MS/MS may be operated in a variety of modes. In one embodiment, the tandem MS/MS spectrometer is operated in an Electrospray Ionization (ESI) mode. In some embodiments, the quantification of the analytes and internal standards is performed in the selected reaction monitoring mode (SRM).

The systems and methods of the present invention may, in certain embodiments, provide for a multiplexed or high throughput assay. For example, certain embodiments of the present invention may comprise a multiplexed liquid chromatography tandem mass spectrometry (LC-MS/MS) or two-dimensional or tandem liquid chromatography-tandem mass spectrometry (LC)-LC-MS/MS) methods for the proteomic analysis.

In some embodiments, a tandem MS/MS system is used. As is known by those of skill in the art, in tandem MS spectrometry, the precursor ion is selected following ionization, and that precursor ion is subjected to fragmentation to generate product (i.e., fragment) ions, whereby one or more product ions are subjected to a second stage of mass analysis for detection. A sample may therefore be analyzed for peptides that correspond to more than one genotype (i.e., for ApoL1, the WT, G1, G2 and common peptides) since the peptides have different precursor and product ions in tandem mass spectrometric methodologies (i.e., different transitions).

The analyte of interest may then be detected based upon the amount of the characteristic transitions measured by tandem MS. In some embodiments, the tandem mass spectrometer comprises a triple quadrupole mass spectrometer. In some embodiments, the tandem mass spectrometer is operated in a positive ion Electrospray Ionization (ESI) mode. Or, other methods of ionization such as Matrix Assisted Laser Desorption/Ionization (MALDI) may be used for ionization. In some embodiments, the detection of the analytes and internal standards is performed in the selected reaction monitoring mode (SRM).

In other embodiments, a surrogate peptide, labeled with a heavy stable isotopes is added to the sample at an appropriate point in the procedure (e.g., prior to digestion) to correct for incomplete digestion and/or sample loss at any step.

The temperature for heating the sample during ionization may, in alternate embodiments range from 100° C. to about 1000° C. and includes all ranges therein. In an embodiment, a dehydration step is performed within the interface of the mass spectrometer employed in electrospray mode at 500 degrees C.±100 degrees. In an embodiment, the sample is heated for several microseconds at the interface for dehydration to occur. In alternate embodiments, the heating step is done for less than 1 second, or less than 100 milliseconds (msec), or less than 10 msec, or less than 1 msec, or less than 0.1 msec, or less than 0.01 msec, or less than 0.001 msec.

FIG. 14 shows an embodiment of a system of the present invention. As shown in FIG. 14, the system may comprise a station for processing a sample (104) that may comprise a biomarker of interest into sampling containers (e.g., 96 well microtiter assay wells). In one embodiment, the sample is aliquoted into a container or containers to facilitate protease digestion and/or enrichment and/or sample dilution. The station for aliquoting may comprise receptacles to discard the portion of the biological sample that is not used in the analysis.

The system may further comprise a station for adding an internal standard to the sample (108). In an embodiment, the internal standard comprises the biomarker of interest labeled with a heavy, stable isotope. Thus, the station for adding an internal standard may comprise safety features to facilitate adding an isotopically labeled internal standard solutions to the sample. The system may also, in some embodiments, comprise a station (110) for enrichment, protein precipitation and/or dilution of the sample.

The system may also comprise a station for liquid chromatography (LC) of the sample. As described herein, in an embodiment, the station for liquid chromatography may comprise an extraction liquid chromatography column (112). The station for liquid chromatography may comprise a column comprising the stationary phase, as well as containers or receptacles comprising solvents that are used as the mobile phase. In an embodiment, the mobile phase comprises a gradient of methanol and water, acetonitrile and water, or other miscible solvents with aqueous volatile buffer solutions. Thus, in one embodiment, the station may comprise the appropriate lines and valves to adjust the amounts of individual solvents being applied to the column or columns. Also, the station may comprise a means to remove and discard those fractions from the LC that do not comprise the biomarker of interest. In an embodiment, the fractions that do not contain the biomarker of interest are continuously removed from the column and sent to a waste receptacle for decontamination and to be discarded.

The system may also comprise an analytical LC column (114). The analytical column may facilitate further purification and concentration of the biomarker of interest as may be required for further characterization and quantification.

Also, the system may comprise a station for characterization and quantification of the allele specific surrogate peptide. In one embodiment, the system may comprise a station for in source ionization (115) and a station for mass spectrometry (MS) (116) of the biomarker. In an embodiment, the station for mass spectrometry comprises a station for tandem mass spectrometry (MS/MS). Also, the station for characterization and quantification may comprise a station for data analysis (118) and/or a computer (102) and software for analysis of the MS/MS results. In an embodiment, the analysis comprises both identification and quantification of the allele specific surrogate peptide.

In some embodiments, one or more of the purification or separation steps can be performed "on-line." As used herein, the term "on-line" refers to purification or separation steps that are performed in such a way that the test sample is disposed, e.g., injected, into a system in which the various components of the system are operationally connected and, in some embodiments, in fluid communication with one another. The on-line system may comprise an autosampler for removing aliquots of the sample from one container and transferring such aliquots into another container. For example, an autosampler may be used to transfer the sample after extraction onto an LC extraction column. Additionally or alternatively, the on-line system may comprise one or more injection ports for injecting the fractions isolated from the LC extraction columns onto the LC analytical column. Additionally or alternatively, the on-line system may comprise one or more injection ports for injecting the LC purified sample into the MS system. Thus, the on-line system may comprise one or more columns, including but not limited to, an extraction column, including an HTLC extraction column, and in some embodiments, an analytical column. Additionally or alternatively, the system may comprise a detection system, e.g., a mass spectrometer system. The on-line system may also comprise one or more pumps; one or more valves; and necessary plumbing. In such "on-line" systems, the test sample and/or analytes of interest can be passed from one component of the system to another without exiting the system, e.g., without having to be collected and then disposed into another component of the system.

In some embodiments, the on-line purification or separation method can be automated. In such embodiments, the steps can be performed without the need for operator intervention once the process is set-up and initiated. Thus, in various embodiments, the system, or portions of the system may be controlled by a computer or computers (102). Thus, in certain embodiments, the present invention may comprise software for controlling the various components of the system, including pumps, valves, autosamplers, and the like. Such software can be used to optimize the extraction process through the precise timing of sample and solute additions and flow rate.

Although some or all of the steps in the method and the stations comprising the system may be on-line, in certain embodiments, some or all of the steps may be performed "off-line." In contrast to the term "on-line", the term "off-line" refers to a purification, separation, or extraction procedure that is performed separately from previous and/or subsequent purification or separation steps and/or analysis steps. In such off-line procedures, the analytes of interests typically are separated, for example, on an extraction column or by liquid/liquid extraction, from the other components in the sample matrix and then collected for subsequent introduction into another chromatographic or detector system. Off-line procedures typically require manual intervention on the part of the operator.

Liquid chromatography may, in certain embodiments, comprise high turbulence liquid chromatography or high throughput liquid chromatography (HTLC). See, e.g., Zimmer et al., J. Chromatogr. A 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. In such columns, separation is a diffusional process. Turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the biomarker of interest prior to mass spectrometry. In such embodiments, samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. Also, in some embodiments, the use of a high turbulence liquid chromatography sample preparation method can eliminate the need for other sample preparation methods including liquid-liquid extraction. Thus, in some embodiments, the test sample, e.g., a biological fluid, can be disposed, e.g., injected, directly onto a high turbulence liquid chromatography system.

For example, in a typical high turbulence or turbulent liquid chromatography system, the sample may be injected directly onto a narrow (e.g., 0.5 mm to 2 mm internal diameter by 20 to 50 mm long) column packed with large (e.g., >25 micron) particles. When a flow rate (e.g., 3-500 mL per minute) is applied to the column, the relatively narrow width of the column causes an increase in the velocity of the mobile phase. The large particles present in the column can prevent the increased velocity from causing back pressure and promote the formation of vacillating eddies between the particles, thereby creating turbulence within the column.

In high turbulence liquid chromatography, the analyte molecules may bind quickly to the particles and typically do not spread out, or diffuse, along the length of the column. This lessened longitudinal diffusion typically provides better, and more rapid, separation of the analytes of interest from the sample matrix. Further, the turbulence within the column reduces the friction on molecules that typically occurs as they travel past the particles. For example, in traditional HPLC, the molecules traveling closest to the particle move along the column more slowly than those flowing through the center of the path between the particles. This difference in flow rate causes the analyte molecules to spread out along the length of the column. When turbulence is introduced into a column, the friction on the molecules from the particle is negligible, reducing longitudinal diffusion.

The methods and systems of the present invention may use mass spectrometry to detect and quantify the biomarker of interest. The terms "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrometer where, due to a combination of electric fields, the ions follow a path in space that is dependent upon mass ("m") and charge ("z").

In certain embodiments, the mass spectrometer uses a "quadrupole" system. In a "quadrupole" or "quadrupole ion trap" mass spectrometer, ions in an oscillating radio frequency (RF) field experience a force proportional to the direct current (DC) potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

In certain embodiments, tandem mass spectrometry is used. See, e.g., U.S. Pat. No. 6,107,623, entitled "Methods and Apparatus for Tandem Mass Spectrometry," which is hereby incorporated by reference in its entirety. Further, the selectivity of the MS technique can be enhanced by using "tandem mass spectrometry," or "MS/MS." Tandem mass spectrometry (MS/MS) is the name given to a group of mass spectrometric methods wherein "parent or precursor" ions generated from a sample are fragmented to yield one or more "fragment or product" ions, which are subsequently mass analyzed by a second MS procedure. MS/MS methods are useful for the analysis of complex mixtures, especially biological samples, in part because the selectivity of MS/MS can minimize the need for extensive sample clean-up prior to analysis. In an example of an MS/MS method, precursor ions are generated from a sample and passed through a first mass filter to select those ions having a particular mass-to-charge ratio. These ions are then fragmented, typically by collisions with neutral gas molecules in a suitable ion containment device, to yield product (fragment) ions, the mass spectrum of which is recorded by an electron multiplier detector. The product ion spectra so produced are indicative of the structure of the precursor ion, and the two stages of mass filtering can eliminate ions from interfering species present in the conventional mass spectrum of a complex mixture.

In an embodiment, the methods and systems of the present invention use a triple quadrupole MS/MS (see e.g., Yost, Enke in Ch. 8 of Tandem Mass Spectrometry, Ed. McLafferty, pub. John Wiley and Sons, 1983). Triple quadrupole MS/MS instruments typically consist of two quadrupole mass filters separated by a fragmentation means. In one embodiment, the instrument may comprise a quadrupole mass filter operated in the RF only mode as an ion containment or transmission device. In an embodiment, the quadrupole may further comprise a collision gas at a pressure of between 1 and 10 millitorr. Many other types of "hybrid" tandem mass spectrometers are also known, and can be used in the methods and systems of the present invention including various combinations of orbitrap analyzers and quadrupole filters. These hybrid instruments often comprise high resolution orbitrap analyzers (see e.g., Hu Q, Noll R J, Li H, Makarov A, Hardman M, Graham Cooks R. The Orbitrap: a new mass spectrometer. J Mass Spectrom. 2005; 40(4):430-443) for the second stage of mass analysis. Use of high resolution mass analyzer may be highly effective in reducing chemical noise to very low levels.

For the methods and systems of the present invention, ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

In those embodiments, such as MS/MS, where precursor ions are isolated for further fragmentation, collision-induced dissociation ("CID") may be used to generate the fragment ions for further detection. In CID, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, to attain the required analytical selectivity and sensitivity, the presently disclosed 2D-LC-MS/MS methods include multiplexed sample preparation procedures. For example, in certain embodiments dialysis of the sample is performed using a 96 well plate having a dialysis membrane in each well or multiple sample tubes. Additionally or alternatively, the multiplex system may comprise staggered multiplexed LC and MS sample inlet systems. Also, the methods and systems of the present invention may comprise multiple column switching protocols, and/or heart-cutting (LC-LC or 2D-LC) techniques, and/or LC separations prior to MS detection. In some embodiments, the methods and systems of the present invention may include a multiplexed two-dimensional liquid chromatographic system coupled with a tandem mass spectrometer (MS/MS) system, for example a triple quadrupole MS/MS system. Such embodiments provide for staggered, parallel sample input into the MS system.

Thus, multiple samples may each be applied to individual extraction columns. Once the samples have each run through the extraction column, they may each be transferred directly (e.g., by column switching) to a second set of analytical columns. As each sample elutes from the analytical column, it may be transferred to the mass spectrometer for identification and quantification.

A plurality of analytes can be analyzed simultaneously or sequentially by the presently disclosed LC-MS/MS and 2D-LC-MS/MS methods. Exemplary analytes amenable to analysis by the presently disclosed methods include, but are not limited to, peptides, steroid hormones, nucleic acids, vitamins and the like. One of ordinary skill in the art would recognize after a review of the presently disclosed subject matter that other similar analytes could be analyzed by the methods and systems disclosed herein. Thus, in alternate embodiments, the methods and systems may be used to quantify steroid hormones, protein and peptide hormones, peptide and protein biomarkers, drugs of abuse and therapeutic drugs. For example, optimization of key parameters for each analyte can be performed using a modular method development strategy to provide highly tuned bioanalytical assays. Thus, certain steps may be varied depending upon the analyte being measured as disclosed herein.

Also, embodiments of the methods and systems of the present invention may provide equivalent sensitivity attainable for many of the analytes being measured using much less sample. For example, through using this optimization procedure, an LLOQ of about 10 nanomoles/L of ApoL1 for dried plasma corresponding to about 20 µL of liquid plasma. Such small sample sizes render sampling (often by fingerprick) much more accessible.

EXAMPLES

Additional data from the analytical validation and standard operating procedures for the presently disclosed method are set forth in the following Examples.

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

LC-MS/MS for ApoL1 Genotyping

Two genetic variants of ApoL1, termed G1 and G2, as well as wild-type alleles were measured by LC-MS/MS.

In addition to standard serum and plasma specimens, the genetic test utilizes specimens acquired on blood collection devices that deposit blood on a substrate. These collection devices provide a metering mechanism that spots a defined volume of blood onto plasma separation strips. This automation is intended to provide an easier sampling mechanism for the patient. Dried blood is an alternate specimen collection process that utilizes a finger stick and a plasma separator strip instead of venipuncture collection of serum or plasma tubes. The functional core of the collection strip is a specialized blood separator material that restricts the migration of cells from the application site while allowing the lateral flow of plasma. This selective migration separates the cells and plasma within the lateral flow material similar to the separation obtained from the centrifugation of a serum separator tube. Dried plasma from a standardized punched section of the separation material can be analyzed in place of liquid plasma or serum using established laboratory procedures.

The three genetic variants of ApoL1—wild-type (WT), G1, and G2—were determined by identifying the corresponding mutations in the protein sequence of ApoL1 circulating in whole blood. This was accomplished by first denaturing the serum or plasma sample, followed by trypsin digestion to produce proteolytic surrogate peptides specific to the three variant forms of ApoL1. The digested plasma was then directly analyzed by LC-MS/MS to determine the presence or absence of the respective surrogate peptides to infer the presence or absence of the associated ApoL1 variant. Two surrogate peptides common among all three ApoL1 variants were also monitored for qualifying sample processing. The presence or absence of the surrogate peptides was determined by comparing the measured responses of the surrogate peptide to the responses of its stable isotope-labeled analogue that was added as an internal standard to sample aliquots prior to trypsin digestion. Based on the pattern of surrogate peptides detected, the genotype of the specimen/individual was determined.

Assay Summary and Surrogate Peptide Specificity

TABLE 1

Surrogate Peptide Specificity

| | |
|---|---|
| Analyte Protein Name: | Human Apolipoprotein L1 |
| Protein Database Reviewed: | UniProt; Homo sapiens (canonical + isoforms); UP000005640, accessed 2018 Feb. 27 |
| Analyte Protein Accession(s): | O14791 |
| Protease (specificity): | Trypsin (R/K\|P) |
| Conserved, Qualifying Surrogate Peptide Sequence(s): | SETAEELK (SEQ ID NO. 7), aa 365-371<br>VAQELEEK (SEQ ID NO. 8), aa 373-380 |

| Variant Protein Nomenclature: | WT (wild-type) | G1* | G2 |
|---|---|---|---|
| DNA Sequence Mutation: | — | 1152T>G | 1169delTTATAA |
| Protein Sequence Mutation: | — | Ile384Met | N388_Y389del |

TABLE 1-continued

Surrogate Peptide Specificity

| Variant-specific Surrogate Peptide Sequences: | LNILNNNYK (SEQ ID NO. 4) aa 382-390 | LNMLNNNYK (SEQ ID NO. 5) aa 382-390 | LNILNNK (SEQ ID NO. 6) aa 382-388 |
|---|---|---|---|
| Surrogate Peptide Modifications: | no annotated PTMs, no annotated sequence variants | | |
| Surrogate Peptide BLAST: | specific to ApoL1, no close alignments require specificity testing | | |

*The G1 risk allele is comprised of two single nucleotide variants 1024A>G (Ser342Gly) and 1152T>G (Ile384Met) which are in near perfect disequilibrium (i.e. occur together in the vast majority of the time). This LC-MS/MS assay does not test for the presence of 1024A>G (Ser342Gly).

Stock Internal Standard Solutions

Stock internal standard material of the following synthetic, stable isotopically-labeled peptides were purchased commercially (New England Peptide) as 0.1 mg (100 μg, net) dry aliquots with amino acid analysis.

TABLE 2

Internal Standard Peptides

| Abbreviation | SEQ ID No. | Sequence | Label(s) |
|---|---|---|---|
| SET | 7 | SETAEEL^K^ (SEQ ID NO. 14) | L^ = [15N, 13C6]-Leucine |
| VAQ | 8 | VAQEL^EEK^ (SEQ ID NO. 15) | K^ = [15N2, 13C6]-Lysine |
| LNI_WT | 4 | L^NILNNNYK^ (SEQ ID NO. 16) | |
| LNM_G1 | 5 | L^NMLNNNYK^ (SEQ ID NO. 17) | |
| LNI_G2 | 6 | L^NILNNK^ (SEQ ID NO. 18) | |

Individual stock internal standard solutions were prepared by adding 0.4 mL of 0.001% zwittergent 3-16 with 0.1% formic acid directly to a single 0.1 mg vial produce a ~200 μg/mL solution. These internal standard stock solutions were allowed to incubate for 15 minutes prior to use and if not used within 4 hours, frozen at −70° C.

Prior to use, the exact concentration of each stock solution was assigned by UV absorbance using a NanoDrop™ 2000c Spectrophotometer at 205 nm, with baseline correction at 340 nm. Each stock was measured on the NanoDrop™ pedestal as at least 10 replicates following blanking with 0.001% zwittergent 3-16 with 0.1% formic acid. The mean absorbance ($A_{205}$) should be between 0.3 and 1.2, with a CV less than 3%, and was used to calculate the stock concentration ($C_{stock}$) based on a path length (b) of 0.1 cm and extinction coefficient ($\varepsilon_{205}$) of 0.031 mL/μg/cm according to the equation below:

$$C_{stock} = \frac{A_{205}}{\varepsilon_{205} \times b}.$$

Control Preparation

Negative Control—the negative control was 30 mg/mL human serum albumin (HSA).

Positive Control The positive control was a pool of male plasma (Golden West Biologicals, Cat #MSG15000M). This control served as positive control for the WT variant and as a "weak positive" control for both the G1 and G2 variants.

WT/G1 EDTA Plasma Control A EDTA plasma specimens from WT/WT, G1/G1, and WT/G1 individuals were pooled to ensure a balanced ratio of G1 and WT variants. This control served as a positive control for both the WT and G1 variants, while serving as a negative control for the G2 variant.

WT/G2 EDTA Plasma Control B EDTA plasma specimens from WT/WT, G2/G2, and WT/G2 individuals were pooled to ensure a balanced ratio of G2 and WT variants. This control served as a positive control for both the WT and G2 variants, while serving as a negative control for the G1 variant.

G1/G2 EDTA Plasma Control C EDTA plasma specimens from G1/G1, G2/G2, and G1/G2 individuals were pooled to ensure a balanced ratio of G1 and G2 variants. This control served as a positive control for both the G1 and G2 variants, while serving as a negative control for the WT variant. At least one replicate of each of the following whole blood QC samples was included in each of the first 20 batches used to establish inter-assay reproducibility as dry punches produced at least 2 hours following deposition of 180 μL onto a lateral flow substrate for separation of dried blood cells from plasma.

WT/G1 LiHep Whole Blood Control A Lithium heparin whole blood specimens from WT/WT, G1/G1, and WT/G1 individuals were pooled to ensure a balanced ratio of G1 and WT variants. This control will served as a positive control for both the WT and G1 variants, while serving as a negative control for the G2 variant.

WT/G2 LiHep Whole Blood Control B Lithium heparin specimens from WT/WT, G2/G2, and WT/G2 individuals were pooled to ensure a balanced ratio of G2 and WT variants. This control served as a positive control for both the WT and G2 variants, while serving as a negative control for the G1 variant.

G1/G2 LiHep Whole Blood Control C Lithium heparin whole blood specimens from G1/G1, G2/G2, and G1/G2 individuals were pooled to ensure a balanced ratio of G1 and G2 variants. This control will serve as a positive control for both the G1 and G2 variants, while serving as a negative control for the WT variant.

Assay Procedure

Controls, samples, digestion buffer, and working internal standards (IS) were thawed at room temperature (20-25° C.). Aliquots (e.g., 20 μL) of controls and samples were pipetted into wells in a 2 mL 96-deep well plate. The negative control received two aliquots. For the dried plasma samples, generally three (3) ¼" diameter punches of dry plasma from the lateral flow substrate were used in place of 20 μL liquid sample. Next, 180 μL digestion buffer (50 mM Tris-HCl, 0.675 mM DTT, 6.75 mg/mL DOC, pH 8.0) was added into each of the wells. The plate wells were then sealed, and after centrifugation for 5-30 seconds, the plate was incubated on the Thermomixer at 56° C. and 1500 rpm for 30 minutes (to allow for denaturation of the proteins and extraction of the dried plasma to occur).

At this point, the internal standards for each of the peptides were added into each well (except for the double negative control which received 20 μL 0.001% Zwittergent 3-16). An aliquot (25 μL) of trypsin solution (32 mg/mL Trypsin in 50 mM Acetic Acid) was added to each well and after sealing each of the wells, the plate was centrifuged for 5-30 seconds, then incubated on the Thermomixer at 37° C. and 1500 rpm for 30 minutes to allow digestion to occur. After digestion is complete (30 min) 1000 μL of Quench Buffer (0.001% (w/v) Zwittergent 3-16 with 2% formic acid) is added into each well. The wells were then sealed with foil and the samples mixed for 1 min at 1500-3500 rpm. After centrifugation (10 min at 3500 rpm) 200 uL of supernatant was transferred into wells in a new 1 mL 96-deep well plate and the samples processed for LC-MS/MS.

HPLC-MS/MS

HPLC was performed using an Aria Transcend TX4 System (Thermo-Fischer) consisting of 8 1200SL Series Binary Pumps and 4 1200 Series Vacuum Degasser and employed a gradient of formic acid in water and acetonitrile. Selected Reaction Monitoring (SRM, i.e., MS/MS) employed a API 5500 Tandem Mass Spectrometer (Sciex, Toronto Canada) and Turbo V™ Ion Source with Electrospray. SRM transitions for the various fragment ions generated are shown below in Table 3. For example, for unlabeled Qualifying Peptide 1, the transition of 453.724→690.367 was measured as the primary transition and the transition of 453.724→217.082 m/z was measured as the secondary transition. As larger molecules (like proteins and peptides) often have more than 1 charge (typically 2 or 3 for a tryptic peptide), it is not uncommon for peptides in Q1 to have a smaller mass (m) to charge (z) ratio (i.e., where z=2), but then lose a charge during fragmentation such that Q3 isolates a larger m/z (i.e., where z=1).

TABLE 3

SRM Transitions

| Q1 Mass (Da) | Q3 Mass (Da) | Dwell (msec) | Param | Value | ID | Primary or Secondary |
|---|---|---|---|---|---|---|
| 453.724 | 690.367 | 50 | DP<br>CE | 64.2<br>20.2 | sp\|O14791\|APOL1_WT.SETAEELK.+2y6.light | primary |
| 453.724 | 217.082 | 5 | DP<br>CE | 64.2<br>20.2 | sp\|O14791\|APOL1_WT.SETAEELK.+2b2.light | secondary |
| 461.240 | 705.398 | 50 | DP<br>CE | 64.2<br>20.2 | sp\|O14791\|APOL1_WT.SETAEELK.+2y6.heavy | primary |
| 461.240 | 217.082 | 5 | DP<br>CE | 64.2<br>20.2 | sp\|O14791\|APOL1_WT.SETAEELK.+2b2.heavy | secondary |
| 473.248 | 846.42 | 5 | DP<br>CE | 65.6<br>21.1 | sp\|O14791\|APOL1_WT.VAQELEEK.+2y7.light | secondary |
| 473.248 | 775.383 | 50 | DP<br>CE | 65.6<br>21.1 | sp\|O14791\|APOL1_WT.VAQELEEK.+2y6.light | primary |
| 480.764 | 861.452 | 5 | DP<br>CE | 65.6<br>21.1 | sp\|O14791\|APOL1_WT.VAQELEEK.+2y7.heavy | secondary |
| 480.764 | 790.415 | 50 | DP<br>CE | 65.6<br>21.1 | sp\|O14791\|APOL1_WT.VAQELEEK.+2y6.heavy | primary |
| 553.304 | 765.389 | 10 | DP<br>CE | 71.5<br>28.6 | sp\|O14791\|APOL1_WT.LNILNNNYK.+2y6.light | primary |
| 553.304 | 652.305 | 30 | DP<br>CE | 71.5<br>24.6 | sp\|O14791\|APOL1_WT.LNILNNNYK.+2y5.light | secondary |
| 560.819 | 773.403 | 10 | DP<br>CE | 71.5<br>28.6 | sp\|O14791\|APOL1_WT.LNILNNNYK.+2y6.heavy | primary |
| 560.819 | 660.319 | 30 | DP<br>CE | 71.5<br>24.6 | sp\|O14791\|APOL1_WT.LNILNNNYK.+2y5.heavy | secondary |
| 562.282 | 896.429 | 10 | DP<br>CE | 72.1<br>25.0 | sp\|O14791\|APOL1_G1.LNMLNNNYK.+2y7.light | secondary |
| 562.282 | 652.305 | 30 | DP<br>CE | 72.1<br>25.0 | sp\|O14791\|APOL1_G1.LNMLNNNYK.+2y5.light | primary |
| 569.798 | 904.444 | 10 | DP<br>CE | 72.1<br>25.0 | sp\|O14791\|APOL1_G1.LNMLNNNYK.+2y7.heavy | secondary |
| 569.798 | 660.319 | 30 | DP<br>CE | 72.1<br>25.0 | sp\|O14791\|APOL1_G1.LNMLNNNYK.+2y5.heavy | primary |

TABLE 3-continued

SRM Transitions

| Q1 Mass (Da) | Q3 Mass (Da) | Dwell (msec) | Param | Value | ID | Primary or Secondary |
|---|---|---|---|---|---|---|
| 414.751 | 375.199 | 10 | DP | 61.4 | sp\|O14791\|APOL1_G2.LNILNNK.+2y3.light | secondary |
|  |  |  | CE | 18.5 |  |  |
| 414.751 | 601.367 | 30 | DP | 61.4 | sp\|O14791\|APOL1_G2.LNILNNK.+2y5.light | primary |
|  |  |  | CE | 22.5 |  |  |
| 422.266 | 723.424 | 10 | DP | 61.4 | sp\|O14791\|APOL1_G2.LNILNNK.+2y6.heavy | secondary |
|  |  |  | CE | 18.5 |  |  |
| 422.266 | 609.381 | 30 | DP | 61.4 | sp\|O14791\|APOL1_G2.LNILNNK.+2y5.heavy | Primary |
|  |  |  | CE | 22.5 |  |  |
| 422.266 | 383.213 | 10 | DP | 61.4 | sp\|O14791\|APOL1_G2.LNILNNK.+2y3.heavy | N/A |
|  |  |  | CE | 18.5 |  |  |

Sanger Sequencing

Sanger sequencing of genomic DNA employed the following primers.

PCR Amplification
ApoL1 F2
(SEQ ID NO. 9)
5'-CGACCTGGTCATCAAAAGCCTTGAC-3'

ApoL1 R2
(SEQ ID NO. 10)
5'-GGAGGCAGAGCTTGCAGTGAGCTG-3'

Sequencing Reaction
ApoL1 F1
(SEQ ID NO. 11)
5'-AGACGAGCCAGAGCCAATC-3'

ApoL1 R1
(SEQ ID NO. 12)
5'-CTGCCAGGCATATCTCTCCT-3'

Genomic DNA was PCR amplified using a 66° C. annealing temperature for 30 cycles. The amplified product was isolated by agarose gel electrophoresis and the DNA treated with Shrimp Alkaline Phosphatase/Exonuclease I for sequencing.

Data Analysis

Following integration of all chromatographic peaks (e.g., within Analyst) the raw analytical responses (peak areas) were processed as follows for each specimen:

1. Divide the response of each surrogate peptide's primary transition by the response of the matching labeled internal standard peptide's primary transition—this is the primary Analyte: Internal Standard peak area ratio (primary PAR).

2. Divide the response of each surrogate peptide's secondary transition by the response of the matching labeled internal standard peptide's secondary transition—this is the secondary Analyte: Internal Standard peak area ratio (secondary PAR).

3. Compare the primary PAR and secondary PAR for each surrogate peptide to the values within the PAR Threshold Table to determine the PAR classifications.

TABLE 4

PAR Threshold Table

|  |  | Qualifying Peptides | | Variant Specific Peptides | | |
|---|---|---|---|---|---|---|
| PAR | Classification | SET | VAQ | LNI_WT | LNM_G1 | LNI_G2 |
| Primary PAR | Detected | ≥0.021 | ≥0.080 | ≥0.043 | ≥0.031 | ≥0.046 |
|  | Indeterminate | — | — | 0.017-0.043 | 0.012-0.031 | 0.018-0.046 |
|  | Undetected | <0.021 | <0.080 | ≤0.017 | ≤0.012 | ≤0.018 |
| Secondary PAR | Detected | ≥0.021 | ≥0.080 | ≥0.043 | ≥0.066 | ≥0.073 |
|  | Indeterminate | — | — | 0.017-0.043 | 0.038-0.066 | 0.028-0.073 |
|  | Undetected | <0.021 | <0.080 | ≤0.017 | ≤0.038 | ≤0.028 |

Based on the pattern of surrogate peptides observed in a specimen (Positive=1, Negative=0), the genotype of the specimen may be defined using the Pattern Table (Table 5). IF the pattern of surrogate peptides detected and undetected in a specimen is not found within the Pattern Table, then the genotype is deemed inconclusive and the extracted specimen may be re-injected and/or the original specimen may be re-extracted. Results were compared to results by Sanger sequencing.

TABLE 5

Pattern Table

|  | Qualifying Peptides | | Variant-Specific Peptides | | |
|---|---|---|---|---|---|
| Genotype | SET | VAQ | LNI_WT | LNM_G1 | LNI_G2 |
| WT/WT | 1 | 1 | 1 | 0 | 0 |
| WT/G1 | 1 | 1 | 1 | 1 | 0 |
| WT/G2 | 1 | 1 | 1 | 0 | 1 |
| G1/G1 | 1 | 1 | 0 | 1 | 0 |
| G2/G2 | 1 | 1 | 0 | 0 | 1 |
| G1/G2 | 1 | 1 | 0 | 1 | 1 |

TABLE 5-continued

Pattern Table

| | Qualifying Peptides | | Variant-Specific Peptides | | |
|---|---|---|---|---|---|
| Genotype | SET | VAQ | LNI_WT | LNM_G1 | LNI_G2 |
| Positive Control | 1 | 1 | 1 | 1 | 1 |
| Negative Control | 0 | 0 | 0 | 0 | 0 |

Example 2—Embodiments

The disclosure may be better understood by referencing the following non-limiting embodiments.

A1. A method for determining a genotype of a gene of interest in a subject, the method comprising:
provihding a body fluid from the subject, the bodily fluid containing a protein derived from the gene of interest;
depositing the body fluid on a solid substrate, wherein the fluid is allowed to dry to produce a dry specimen;
digesting the dry specimen to generate at least one allele specific surrogate peptide for the protein;
using mass spectrometry to detect the at least one allele specific surrogate peptide present in the digested sample; and
determining the genotype of the subject based on the presence or absence or amount of the at least one allele specific surrogate peptide.

A2. The method of any of the previous or subsequent embodiments, wherein the step of digesting is performed with the protease trypsin.

A3. The method of any of the previous or subsequent embodiments, wherein the dry specimen containing the protein derived from the gene of interest is denatured prior to digestion.

A4. The method of any of the previous or subsequent embodiments, wherein the at least one allele specific surrogate peptide is analyzed by liquid chromatography tandem mass spectrometry (LC-MS/MS).

A5. The method of any of the previous or subsequent embodiments, further comprising measuring the amount of at least one common surrogate peptide that is common to each genotype of the gene of interest.

A6. The method of any of the previous or subsequent embodiments, wherein the presence or absence of the at least one allele-specific surrogate peptide is determined by comparing a measured response for at least one allele-specific surrogate peptide to a measured response for at least one common surrogate peptide.

A7. The method of any of the previous or subsequent embodiments, wherein the presence or absence of the at least one allele specific surrogate peptide is determined by comparing a measured response for the at least one allele specific surrogate peptide to a measured response for a stable isotope-labeled analogue of the at least one allele specific surrogate peptide.

A8. The method of any of the previous or subsequent embodiments, wherein the presence or absence of the at least one common surrogate peptide is determined by comparing a measured response for the at least one common surrogate peptide to a measured response for a stable isotope-labeled analogue of the at least one common surrogate peptide.

A9. The method of any of the previous or subsequent embodiments, wherein the stable isotope-labeled analogue of the at least one allele specific surrogate peptide is added as an internal standard.

A10. The method of any of the previous or subsequent embodiments, wherein the stable isotope-labeled analogue of the at least one common surrogate peptide is added as an internal standard.

A11. The method of any of the previous or subsequent embodiments, wherein the measured response of the allele specific surrogate peptide is normalized to the measured response of the stable isotope-labeled analogue of the at least one allele specific surrogate peptide.

A12. The method of any of the previous or subsequent embodiments, wherein the measured response of the common surrogate peptide are normalized to the measured response of the stable isotope-labeled analogue of the at least one common surrogate peptide.

A13. The method of any of the previous or subsequent embodiments, wherein the internal standard for the allele specific surrogate peptide is added prior to the step of digestion.

A14. The method of any of the previous or subsequent embodiments, wherein the internal standard for the common surrogate peptide is added prior to the step of digestion.

A15. The method of any of the previous or subsequent embodiments, wherein the measured response is the peak area ratio for a MS/MS transition characteristic of at least one fragment ion generated from the allele specific surrogate peptide.

A16. The method of any of the previous or subsequent embodiments, wherein the measured response is the peak area ratio for a MS/MS transition characteristic of at least one fragment ion generated from the common surrogate peptide.

A17. The method of any of the previous or subsequent embodiments, wherein the protein is ApoL1.

A18. The method of any of the previous or subsequent embodiments, wherein the allele specific surrogate peptide has the amino acid sequence LNILNNNYK (SEQ ID NO. 4) derived from the wild-type allele (SEQ ID NO. 1), or has the amino acid sequence LNMLNNNYK (SEQ ID NO. 5) derived from the G1 allele (SEQ ID NO. 2), or has the amino acid sequence LNILNNK (SEQ ID NO. 6) derived from the G2 allele (SEQ ID NO. 3).

A19. The method of any of the previous or subsequent embodiments, further comprising determining the amount of a common surrogate peptide having the amino acid sequence of SETAEELK (SEQ ID NO. 7) or VAQELEEK (SEQ ID NO. 8) wherein the common surrogate peptide is present in each of the wild-type, G1 or G2 alleles.

A20. The method of any of the previous or subsequent embodiments, wherein the mass spectrometry measures at least one of the transitions in Table 3.

A21. The method of any of the previous or subsequent embodiments, wherein the presence or absence of the at least one allele specific surrogate peptide is determined by comparing a measured response for the at least one allele specific surrogate peptide to a measured response for a stable isotope-labeled analogue listed in Table 2 of the at least one allele specific surrogate peptide.

A22. The method of any of the previous or subsequent embodiments, wherein the liquid chromatography comprises high performance liquid chromatography (HPLC).

A23. The method of any of the previous or subsequent embodiments, wherein the dried specimen is dried plasma from separated whole blood.

A24. The method of any of the previous or subsequent embodiments, wherein the dried specimen is dried red blood cells from separated whole blood.

A25. The method of any of the previous or subsequent embodiments, wherein the dried specimen is at least one of dried blood, dried urine or dried saliva.

B1. A system for determining the genotype of a gene of interest in a subject, the system comprising:
 a device for providing and drying a body fluid comprising a protein derived from the gene of interest;
 a station for subjecting the dry body fluid to digestion to generate at least one allele specific surrogate peptide and optionally, at least one common surrogate peptide for the protein;
 optionally, a station for chromatographic purification of the at least one allele specific surrogate peptide and the optional at least one common surrogate peptide; and
 a station for analyzing the at least one allele specific surrogate peptide by mass spectrometry to determine the presence or amount of the at least one allele specific surrogate peptide in the biological sample.

B2. The system of any of the previous or subsequent embodiments, wherein the device for providing a biological sample comprises a device to immobilize and separate red blood cells from plasma on a substrate.

B3. The system of any of the previous or subsequent embodiments, further comprising a station for adding a stable isotope labeled internal standard for the at least one allele specific surrogate peptide and optionally, at least one common surrogate peptide for the protein B4. The system of any of the previous or subsequent embodiments, wherein the station for mass spectrometry comprises a tandem mass spectrometer.

B5. The system of any of the previous or subsequent embodiments, wherein the station for chromatography comprises high performance liquid chromatography (HPLC)

B6. The system of any of the previous or subsequent embodiments, wherein at least one of the stations is controlled by a computer.

B7. The system of any of the previous or subsequent embodiments, wherein the protein is ApoL1.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCE TO A SEQUENCE LISTING
SUBMITTED AS A TEXT FILE VIA EFS-WEB

The official copy of the sequence listing is submitted electronically via EFS-Web as an ASCII formatted sequence listing with a file named 1139048_ST25.txt, created on Jun. 23, 2019, and having a size of 14.0 kilobytes. The sequence listing contained in this ASCII formatted document is part of the specification and is herein incorporated by reference in its entirety.

That which is claimed:

1. A method for determining a genotype of a gene of interest in a subject, the method comprising:
   separating on a solid substrate blood obtained from the subject into blood cells and plasma;
   allowing the plasma to dry on the solid substrate, thereby generating a dried plasma sample containing a protein derived from the gene of interest;
   digesting the dried plasma sample with trypsin, in digestion buffer to generate at least one allele specific surrogate peptide for the protein, thereby generating a digested sample;
   using mass spectrometry, detecting the at least one allele specific surrogate peptide in the digested sample; and
   determining the genotype of the subject based on results of the detecting the at least one allele specific surrogate peptide.

2. The method of claim 1, wherein the dried plasma sample containing the protein derived from the gene of interest is subjected to denaturation prior to the digesting.

3. The method of claim 1, wherein the mass spectrometry is tandem mass spectrometry.

4. The method of claim 3, wherein the tandem mass spectrometry is liquid chromatography tandem mass spectrometry (LC-MS/MS).

5. The method of claim 1, further comprising detecting in the digested sample, using the mass spectrometry, at least one common surrogate peptide that is common to each genotype of the gene of interest.

6. The method of claim 5, wherein the detecting the at least one common surrogate peptide comprises acquiring a measured response for the at least one common surrogate peptide.

7. The method of claim 6, wherein the measured response for the at least one common surrogate peptide is a peak area ratio for a MS/MS transition characteristic of at least one fragment ion generated from the at least one common surrogate peptide.

8. The method of claim 6, wherein presence or absence of the at least one common surrogate peptide is determined by comparing the measured response for the at least one common surrogate peptide to a measured response for a stable isotope-labeled analogue of the at least one common surrogate peptide.

9. The method of claim 6, wherein the detecting the at least one allele specific surrogate peptide in the digested sample comprises acquiring a measured response for the at least one allele specific surrogate peptide, and wherein presence or absence of the at least one allele specific surrogate peptide in the digested sample is determined by comparing the measured response for the at least one allele specific surrogate peptide to the measured response for the at least one common surrogate peptide.

10. The method of claim 6, wherein presence or absence of the at least one common surrogate peptide in the digested sample is determined by comparing the measured response for the at least one common surrogate peptide to a measured response for a stable isotope-labeled analogue of the at least one common surrogate peptide.

11. The method of claim 1, wherein the detecting the at least one allele specific surrogate peptide comprises acquiring a measured response for the at least one allele specific surrogate peptide.

12. The method of claim 11, wherein the measured response for the at least one allele specific surrogate peptide is a peak area ratio for a MS/MS transition characteristic of at least one fragment ion generated from the allele specific surrogate peptide.

13. The method of claim 11, wherein presence or absence of the at least one allele specific surrogate peptide in digested sample is determined by comparing the measured response for the at least one allele specific surrogate peptide to the measured response for the at least one common surrogate peptide.

14. The method of claim 11, wherein presence or absence of the at least one allele specific surrogate peptide in the dried plasma sample is determined by comparing the measured response for the at least one allele specific surrogate peptide to a measured response for a stable isotope-labeled analogue of the at least one allele specific surrogate peptide.

15. The method of claim 1, wherein the detecting the at least one allele specific surrogate peptide comprises detecting an amount of the at least one allele specific surrogate peptide.

16. A method for determining a genotype of a subject, the method comprising:
providing a dried plasma sample, wherein the dried plasma sample is deposited on a solid substrate and comprises dried plasma obtained from the subject and separated from red blood cells on the solid substrate prior to allowing the separated plasma to dry;
digesting the dried plasma sample with trypsin in digestion buffer to generate a plurality of allele specific surrogate peptides for protein variants contained in the dried plasma, thereby generating a digested sample;
using mass spectrometry, detecting the plurality of the allele specific surrogate peptides in the digested sample to generate a proteomic profile of the allele specific surrogate peptides; and
determining the genotype of the subject based on the proteomic profile.

17. A system for determining genotype of a gene of interest in a subject, the system comprising:
a device for separating blood obtained from the subject into red blood cells and plasma on a solid substrate, and allowing the plasma to dry on the solid substrate, thereby generating a dried plasma sample;
a station for subjecting the dried plasma sample to digestion by trypsin in digestion buffer to generate at least one allele specific surrogate peptide for a protein derived from the gene of interest, wherein the dried plasma sample is deposited on a solid substrate, is produced by separating plasma from red blood cells on the solid substrate, and comprises dried plasma separated from the red blood cells;
optionally, a station for chromatographic purification of the at least one allele specific surrogate peptide;
a station for analyzing the at least one allele specific surrogate peptide by mass spectrometry to detect the at least one allele specific surrogate peptide; and,
a station for determining the genotype of the gene of interest based on results of the of the at least one allele specific surrogate peptide.

18. The system of claim 17, wherein the station for analyzing the at least one allele specific surrogate peptide by mass spectrometry comprises a tandem mass spectrometer.

19. The system of claim 18, further comprising a station separating the plasma from the red blood cells on the solid substrate.

20. The method of claim 1, wherein the protein is ApoL1, and the allele specific surrogate peptide has amino acid sequence LNILNNNYK (SEQ ID NO. 4) derived from wild-type allele (SEQ ID NO. 1), or has amino acid sequence LNMLNNNYK (SEQ ID NO. 5) derived from G1 allele (SEQ ID NO. 2), or has amino acid sequence LNILNNK (SEQ ID NO. 6) derived from G2 allele (SEQ ID NO. 3).

* * * * *